US012135942B1

(12) United States Patent
Nudd et al.

(10) Patent No.: US 12,135,942 B1
(45) Date of Patent: *Nov. 5, 2024

(54) CONVERSATION FACILITATION SYSTEM FOR MITIGATING LONELINESS

(71) Applicant: ClearCare, Inc., San Francisco, CA (US)

(72) Inventors: Geoffrey Nudd, San Francisco, CA (US); David Cristman, San Francisco, CA (US); John Taylor, San Francisco, CA (US); Jonathan J. Hull, San Carlos, CA (US)

(73) Assignee: CLEARCARE, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/492,239

(22) Filed: Oct. 23, 2023

Related U.S. Application Data

(63) Continuation of application No. 17/402,990, filed on Aug. 16, 2021, now Pat. No. 11,803,708, which is a
(Continued)

(51) Int. Cl.
*G06F 40/00* (2020.01)
*G06F 40/295* (2020.01)
(Continued)

(52) U.S. Cl.
CPC ............ *G06F 40/30* (2020.01); *G06F 40/295* (2020.01); *G06N 3/044* (2023.01); *G06N 3/08* (2013.01);
(Continued)

(58) Field of Classification Search
CPC ...... G06F 40/30; G06F 40/268; G06F 40/284; G06F 40/211; G06F 40/253; G10L 15/07;
(Continued)

(56) References Cited

U.S. PATENT DOCUMENTS 6,598,020 B1   7/2003   Kleindienst et al.
8,374,865 B1   2/2013   Biadsy et al.
(Continued)

FOREIGN PATENT DOCUMENTS

AU    2009202262 A1   12/2009
WO    2013033655 A1   3/2013

OTHER PUBLICATIONS

Aylaz et al., "Relationship Between Depression and Loneliness in Elderly and Examination of Influential Factors", US National Library of Medicine National Institutes of Health, https://www.ncbi.nlm.nih.gov/pubmed/22487148, Apr. 8, 2012, 2 pgs.
(Continued)

*Primary Examiner* — Vu B Hang
(74) *Attorney, Agent, or Firm* — PATENT LAW WORKS LLP

(57) ABSTRACT

The present disclosure describes a conversation facilitation system for facilitating conversation-based social interactions to improve senior health, one or more operations and functions being efficiently achieved via this system comprise: receiving a dialog act of a conversation, applying natural language understanding (NLU) processing on the dialog act, computing a conversation metric, and generating a result of the conversation to conclude the conversation based on the conversation metric.

16 Claims, 27 Drawing Sheets

Related U.S. Application Data continuation of application No. 16/272,037, filed on Feb. 11, 2019, now Pat. No. 11,120,226.

(60) Provisional application No. 62/769,220, filed on Nov. 19, 2018, provisional application No. 62/726,883, filed on Sep. 4, 2018.

(51) Int. Cl.
    *G06F 40/30*     (2020.01)
    *G06N 3/044*     (2023.01)
    *G06N 3/08*     (2023.01)
    *G06F 40/284*     (2020.01)
    *G10L 15/18*     (2013.01)
    *G10L 15/183*     (2013.01)

(52) U.S. Cl.
    CPC ........ *G06F 40/284* (2020.01); *G10L 15/1822* (2013.01); *G10L 15/183* (2013.01)

(58) Field of Classification Search
    CPC ......... G10L 15/20; G10L 15/22; G10L 15/26; G10L 15/30; G10L 15/02; G10L 15/063; G10L 15/08; G10L 15/1822; G10L 15/183; G10L 15/19; G10L 15/193; G10L 15/197; G10L 15/14; G10L 15/1815; G10L 15/16; G10L 19/00; G10L 19/005; G10L 25/27; G10L 25/30
    See application file for complete search history.

(56) References Cited

U.S. PATENT DOCUMENTS

| | | |
|---|---|---|
| 9,723,149 B2 | 8/2017 | Meng et al. |
| 9,798,343 B2 | 10/2017 | Kaufman |
| 9,934,780 B2 | 4/2018 | Tzirkel-Hancock |
| 10,235,990 B2 | 3/2019 | Corelli et al. |
| 10,311,869 B2 | 6/2019 | Weng et al. |
| 10,311,980 B2 | 6/2019 | Kim et al. |
| 10,319,477 B1 | 6/2019 | Bill |
| 10,329,784 B1 | 6/2019 | Corwin |
| 10,543,137 B2 | 1/2020 | Hayes |
| 11,120,226 B1 | 9/2021 | Nudd |
| 11,631,401 B1 | 4/2023 | Nudd |
| 11,633,103 B1 | 4/2023 | Nudd |
| 11,803,708 B1 * | 10/2023 | Nudd ..................... G16H 20/70 |
| 2003/0114736 A1 | 6/2003 | Reed |
| 2003/0200142 A1 | 10/2003 | Hicks |
| 2008/0235018 A1 | 9/2008 | Eggen et al. |
| 2009/0256710 A1 | 10/2009 | Duckert et al. |
| 2009/0307025 A1 | 12/2009 | Menon |
| 2011/0125844 A1 | 5/2011 | Collier et al. |
| 2014/0067730 A1 | 3/2014 | Kozloski |
| 2014/0163337 A1 | 6/2014 | Horseman |
| 2014/0377727 A1 | 12/2014 | Yom-Tov et al. |
| 2016/0198047 A1 | 7/2016 | McCormack |
| 2016/0287166 A1 | 10/2016 | Tran |
| 2018/0075763 A1 | 3/2018 | Wainfan |
| 2018/0226076 A1 | 8/2018 | Kotti et al. |
| 2018/0294059 A1 | 10/2018 | Savant et al. |
| 2018/0308487 A1 | 10/2018 | Goel et al. |
| 2018/0357286 A1 | 12/2018 | Wang et al. |
| 2019/0008583 A1 | 1/2019 | Gallagher et al. |
| 2019/0130243 A1 | 5/2019 | Penubothula et al. |
| 2019/0189253 A1 | 6/2019 | Kartoun |

OTHER PUBLICATIONS

Vargheese et al., "Persuasive Strategies for Encouraging Social Interaction for Older Adults", International Journal of Human-Computer Interaction, vol. 32, 2016—Issue 3, https://www.landfonline.com/doi/full/10.1080/10447318.2016.1136176, Jan. 4, 2016, 6 pgs.

Ring et al., "Addressing Loneliness and Isolation in Older Adults: Proactive Affective Agents Provide Better Support," 2013 Humaine Association Conference on Affective Computing and Intelligent Interaction, Geneva, https://ieeexplore.eee.org/documenl/6681408/citations?labFiller=papers#citations, 2013, 6 pgs.

Reddit "I Have Every Publicly Available Reddit Comment", hllps://www.reddit.com/r/dalasels/commenls/3bxlg7/_have_every_publicly_available_reddit_comment/, ca. 2015, 5 pgs.

Unknown, "Language-Independent Named Entity Recognition (II)," 2003, retrieved online from https://www.clips.uantwerpen.be/conill2003/ner/, Apr. 8, 2019, 7 pgs.

Vargheese et al., "Persuasive Dialogue for Older Adults," CHI 2013 Changing Perspectives, Paris, France, Apr. 27-May 2, 2013, 6 pgs.

Manning et al., "The Stanford CoreNLP Natural Language Processing Toolkit," Proceedings of 52nd Annual Meeting of the Association for Computational Linguistics: System Demonstrations, Jun. 23-24, 2014, pp. 55-60.

Petersen et al., "Unobtrusive in-home detection of time spent out-of-home with applications to loneliness and physical activity", IEEE J Biomed Health Inform, Sep. 2014, 17 pgs.

Asatryan, "4 Disorders That May Thrive on Loneliness", https://www.psychologytoday.com/us/blog/the-art-closeness/201507/4-disorders-may-thrive-loneliness, Jul. 23, 2015, 5 pgs.

Lowe et al., "The Ubuntu Dialogue Corpus: a Large Dataset for Research in Unstructured Multi-Tum Dialogue Systems", School of Computer Science, McGill University, Montreal, Canada, https://arxiv.org/abs/1506.08909, Feb. 4, 2016, 10 pgs.

Baez et al., "Personalized Persuasion for Social Interactions in Nursing Homes", Proceedings of the Personalization ir Persuasive Technology Workshop, Persuasive Technology 2016, Salzburg, Austria, http://ceur-ws.org/Vol-1582/11Baez.pdf, May 4, 2016, 6 pgs.

Chiu et al., "Named Entity Recognition with Bidirectional LSTM-CNNs", Transactions of the Association for Computational Linguistics, vol. 4, Jul. 2016, pp. 357-370.

Bansal, "Beginners Guide to Topic Modeling in Python", Analytics Vidhya, https://www.analyticsvidhya.com/blog/2016/08/beginners-guide-lo-lopic-modeling-in-python/, Aug. 24, 2016, 8 pgs.

Petersen et al., "Phone behaviour and its relationship to loneliness", Aging Ment Health, https://www.ncbi.nlm.nih.gov/pmc/articles/PMC4698244/, Oct. 2016, 16 pgs.

Shao et al., "Generating High-Quality and Informative Conversation Responses", Jul. 31, 2017, 11 pgs.

Chen et al., "Gunrock: Building a Human-Like Social Bot by Leveraging", 2nd Proceedings of Alexa Prize {Alexa Prize J018), Department of Computer Science, University of California, Davis, https://s3.amazonaws.com/dex-microsites-Jrod/alexaprize/2018/papers/Gunrock.pdf, 2018, 19 pgs.

Nemecek, "Cigna's U.S. Loneliness Index", https://www.multivu.com/players/English/8294451-cigna-us-loneliness-survey/, May 2018, 61 pgs.

Lardieri, "Study: Many Americans Report Feeling Lonely, Younger Generations More So", US News & World Report, https://www.usnews.com/news/health-care-news/articles/2018-05-01/sludy-many-americans-report-feeling-onely-younger-generalions-more-so, May 1, 2018, 6 pgs.

An Always on Relational Agent for Social Support, Relational Agents Group, Jan. 9, 2019, 1 pg.

Bird et al., "Natural Language Processing with Python: Chapter 5 Categorizing and Tagging Words", https://www.nltk.org/book/ch05.html, Apr. 1, 2019, 29 pgs.

"Topic Modeling with Gensim {Python)", https://www.machineleamingplus.com/nlp/topic-modeling-gensim-python/, 2018, 43 pgs.

Austin et al., "A Smart-Home System to Unobtrusively and Continuously Assess Loneliness in Older Adults," IEEE Journal of Translational Engineering in Health and Medicine, Jun. 10, 2016, vol. 4, 11 pgs.

Buchman et al., "Loneliness and the rate of motor decline in old age: the rush memory and aging project, a :: community-based cohort study," BMC Geriatrics, 2010, vol. 10, No. 77, 8 pgs.

(56) References Cited

OTHER PUBLICATIONS

Fetzer Institute, "UCLA Loneliness Scale," Self Report Measures for Love and Compassion Research: Loneliness and Interpersonal Problems, at least as early as Feb. 16, 2019, 2 pgs.

Hawkley et al., "Loneliness Predicts Reduced Physical Activity: Cross-Sectional & Longitudinal Analyses," Health Psychol., May 2009, vol. 28, No. 3, pp. 354-363.

Hayes et al., "Unobtrusive assessment of activity patterns associated with mild cognitive impairment," Alzheimers Dement., Nov. 2008, vol. 4, No. 6, pp. 395-405.

Hughes et al., "A Short Scale for Measuring Loneliness in Large Surveys: Results From Two Population-Based Studies," Res. Aging, 2004, vol. 26, No. 6, pp. 655,672.

Kaye et al., "Unobtrusive measurement of daily computer use to detect mild cognitive impairment," Alzheimers Dement., Jan. 2014, vol. 10, No. 1, 15 pgs.

Petersen et al., "SVM to Detect the Presence of Visitors in a Smart Home Environment," Cont. Proc. IEEE Eng. Med. Biol. Soc., 2012, 9 pgs.

Petersen et al., "Phone behaviour and its relationship to loneliness in older adults," Aging Men !. Health, Oct. 2016, vol. 20, No. 10, pp. 1084-1091.

Russell, "UCLA Loneliness Scale {Version 3): Reliability, Validity, and Factor Structure," Journal of Personality Assessment, 1996, vol. 66, No. 1, pp. 20-40.

Glascock et al., The Impact of Behavioral Monitoring Technology on the Provision of Health Care in the Home, 2006, Journal of Universal Computer Science, vol. 12, No. 1 (2006), 59-79 (Year: 2006).

\* cited by examiner

| Initiate | New conversation |
|---|---|
| Senior | Mary Smith |
| Scheduled start date | Sept. 2, 2018 11:00 AM |
| Next scheduled start date | Sept. 3, 2018 1:05 PM |
| Duration | 10 minutes |
| Prescribed recurrence frequency | Daily Mon. through Fri. |
| Requestor | Dr. Patty |
| Requestor category | Physician |
| Prescribed duration | 30 minutes |
| Prescribed extent | 6 months |
| Participants | Compatibility( topic, experience, characteristics ) |
| Questions | Would you like to chat with others?<br>How many people would you like to talk with?<br>What topics would you like to discuss? We can help find people who know about soap operas, movies, football, tennis, baseball, knitting, bridge, soccer, local news, politics, etc.<br>How many years familiarity should the participants have with the topic?<br>What should be age and gender of participants? (female, male, both) |
| Result format | Ascent, topic, familiarity, gender |

Figure 5

| Soap Opera | Young and Restless |
|---|---|
| Senior | Mary Smith |
| Next Scheduled start date | Sept. 3, 2018 1:05 PM |
| Duration | 30 minutes |
| Recurrence frequency | Daily Mon. through Fri. |
| Participants | Mary Smith, Joan Jones, Edwina Edwards, Mike Mellow |
| Requestor | Dr. Patty |
| Requestor category | physician |
| Questions | What do you think x [Katherine Chancellor, Jill Foster Abbott, Jack Abbott, Nicky, Victor, Victoria, Brad,...] will do next? Where did X go? Who is Victoria's real father? |
| External sources | imdb.com, www.cbs.com/shows/the_young_and_the_restless/ |
| Result format | Length, participants, percent participation, tone, joke response |
| External contacts | Participants, date, duration |

Figure 6

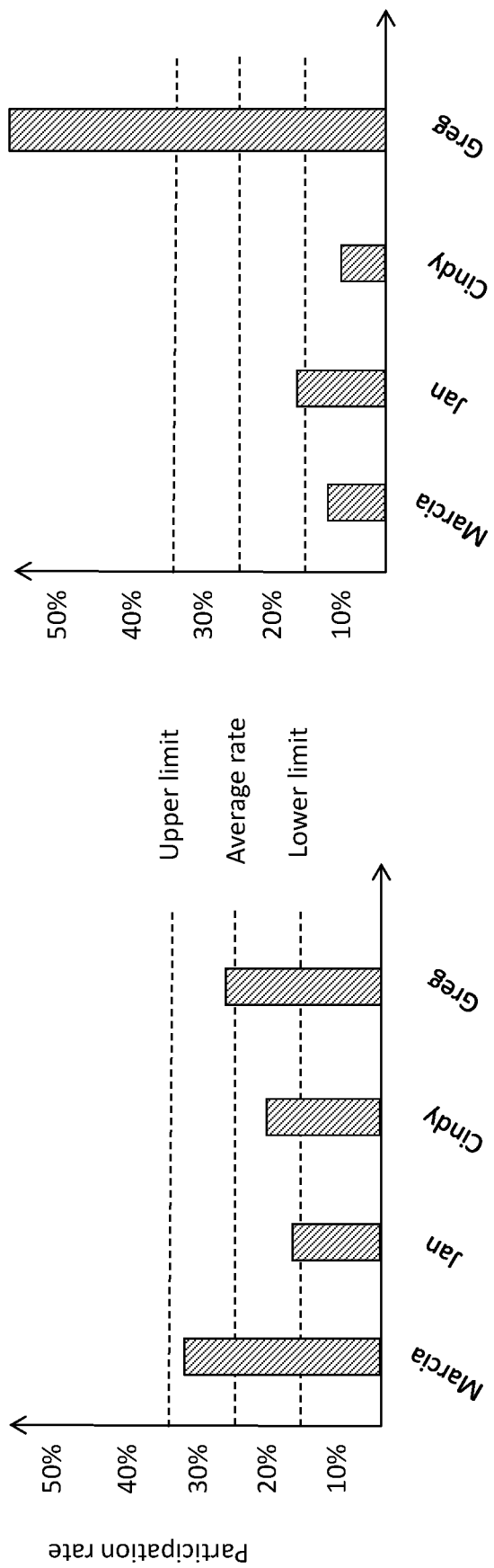
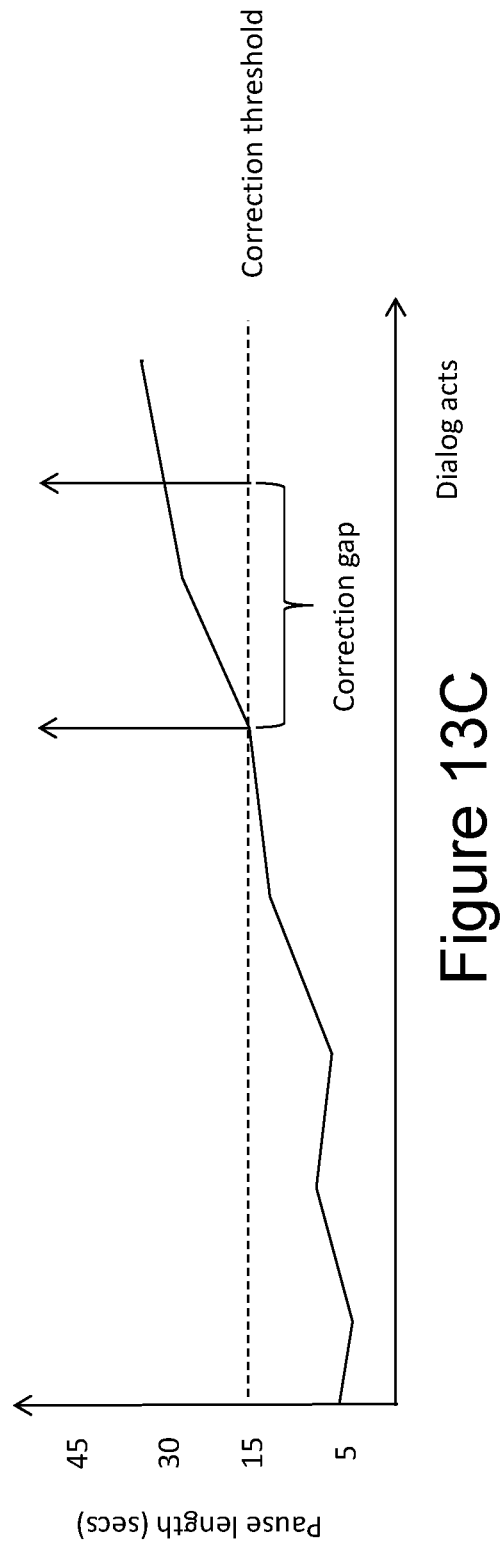
Figure 13A
Figure 13B
Figure 13C

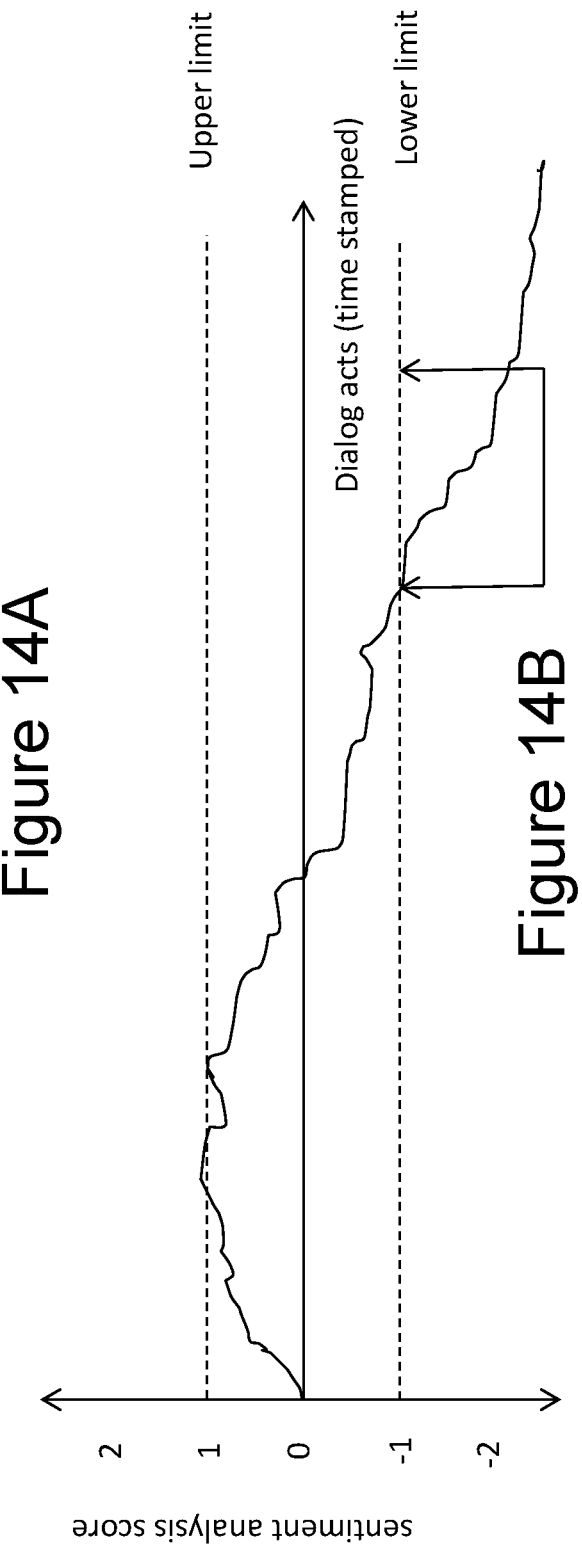

CONVERSATION FACILITATION SYSTEM FOR MITIGATING LONELINESS

CROSS REFERENCE TO RELATED APPLICATIONS

This application is a continuation of U.S. patent application Ser. No. 17/402,990, filed Aug. 16, 2021, entitled "Conversation Facilitation System for Mitigating Loneliness", which is a continuation of U.S. patent application Ser. No. 16/272,037, filed Feb. 11, 2019, entitled "Conversation Facilitation System for Mitigating Loneliness", which application claims the benefit of U.S. Provisional Application No. 62/769,220, filed Nov. 29, 2018, entitled "Senior Care Socialization And Monitoring System", and U.S. Provisional Application No. 62/726,883, filed Sep. 4, 2018, entitled "Conversation-Based System for Mitigating Loneliness", all of which are hereby incorporated by reference in their entirety.

FIELD OF THE INVENTION

The present disclosure relates to supporting seniors in independent living arrangements through technology-assisted managed socialization and monitoring. In particular, the present disclosure relates to a conversation facilitation system for facilitating conversation-based social interactions to improve senior health.

BACKGROUND

Social isolation among people, especially seniors, represents a significant societal challenge. In a typical application, a senior living alone is socially isolated and suffers from psychological and physical ailments attributable to the lack of regular interaction with other people. Family involvement, for example, maintaining an emotional bond through visits and family updates, is important but may be impractical. Therefore, when different physical, psychological, and contextual factors influence the opportunities and motivations of a senior/user himself/herself to interact with others, as well as outside social assistance(s) is hard to obtain, there is a need of a convenient, highly efficient, and smart healthcare management platform that motivates, supports, and facilitates social interactions among seniors/users via networked computing devices to mitigate loneliness and improves health.

SUMMARY

The techniques introduced herein overcome the deficiencies and limitations of the prior art at least in part by providing systems and methods for managed socialization and monitoring to improve senior care.

The techniques introduced herein describe a system architecture and components that mitigate loneliness among senior citizens by proactively initiating conversations over networked devices that support two-way audio and/or video discussions. Conversations with a senior/user are scheduled at the request of a family member or a health care professional. Participants in the conversation are chosen with a compatibility function that determines a group of people who will likely relate well to one another. Conversations are initiated, and proactive interventions or corrections are automatically provided that facilitate social interchange among the participants. At an appropriate time, based on a schedule and/or on the course of the discussion, the conversation is automatically concluded and the requestor is notified.

In some embodiments, a networked device, typically a smart speaker, is installed in the senior's home and interfaced with the proposed system. At regular intervals the system engages the senior in conversations with other people who have similar backgrounds. Over time, the senior develops relationships with those people and has continuing discussions about topics of common interest. The system monitors the development of these relationships and facilitates further conversations with other people as needed.

The various embodiments advantageously apply the teachings of in-home voice-based virtual assistants, social compatibility applications, and health support systems, such as caregiver management platforms. The various embodiments include operations to overcome or at least reduce the issues in the previous socialization systems discussed above and, accordingly, are more efficient and reliable for improving the lives and health outcomes of seniors. That is, the various embodiments disclosed herein include hardware and/or software with functionality to improve the monitoring, management, and processing of socialization data. Accordingly, the embodiments disclosed herein provide various improvements to health support systems targeting seniors.

According to one innovative aspect of the subject matter in this disclosure, a computer-implemented method comprising: receiving, with one or more processors, a dialog act of a conversation, applying, with the one or more processors, natural language understanding (NLU) processing on the dialog act, computing, with the one or more processors, a conversation metric, and generating, with the one or more processors, a result of the conversation to conclude the conversation based on the conversation metric.

Other implementations of one or more of these aspects include corresponding systems, apparatus, and computer programs, configured to perform the actions of the methods, encoded on computer storage devices.

These and other implementations may each optionally include one or more of the following features. For instance, applying the natural language understanding processing on the dialog act may include performing named entity recognition training on the dialog act, and performing topic classifier training on the dialog act; performing the named entity recognition training on the dialog act may comprise training a long short term memory model to assign an entity included in the dialog act with a tag; performing the named entity recognition training on the dialog act may include computing a category score based on biasing a personal relationship known to a participant of the conversation; performing the topic classifier training on the dialog act is based on a web search for a set of documents that reflects a topic of the conversation; also applying sentiment analysis on the dialog act, and wherein computing the conversation metric is based on the sentiment analysis; further comprising tracking a topic of the conversation, tracking mood of a participant of the conversation, and generating a conversation prompt based on the tracking; wherein the conversation is at least one of a proactive conversation and a reactive conversation; notifying a requestor of the result of the conversation when the conversation is a proactive conversation; and wherein the dialog act is a time-stamped data element of the conversation that contains at least one of audio data, video data, or text data that has been recognized.

It should be understood that language used in the present disclosure has been principally selected for readability and instructional purposes, and not to limit the scope of the subject matter disclosed herein.

BRIEF DESCRIPTION OF THE DRAWINGS

The present disclosure is illustrated by way of example, and not by way of limitation in the figures of the accompanying drawings in which like reference numerals are used to refer to similar elements.

FIG. 5 is an example setup proactive conversation object.

FIG. 6 is an example of a proactive conversation object updated based on the setup proactive conversation object as depicted in FIG. 5.

FIGS. 13A-13C are example graphs of conversation metrics.

FIGS. 14A and 14B is an example result from tracking the discussed topics and mood of participants in a conversation.

DETAILED DESCRIPTION

The present disclosure describes systems and methods for facilitating conversations among seniors to improve senior health. In the following descriptions, for purpose of explanation, numerous specific details are set forth in order to provide a thorough understanding of the present disclosure. However, it should be noted that the present disclosure might be practiced without these specific details.

Figure 1:
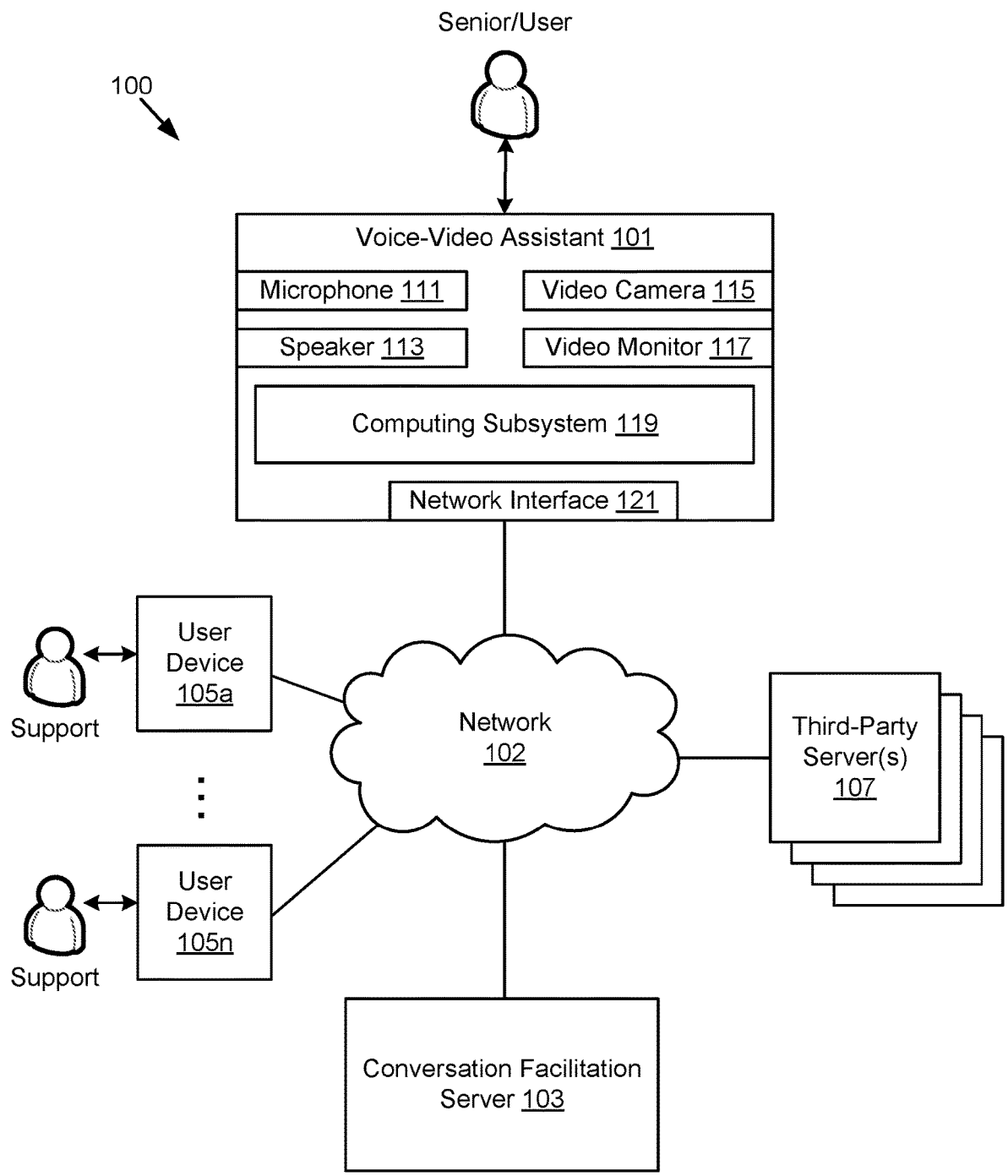
FIG. 1 is a block diagram illustrating an example conversation facilitation system for facilitating conversations among seniors.

FIG. 1 is a block diagram illustrating an example conversation facilitation system 100 for facilitating conversations among seniors. As illustrated, the conversation facilitation system 100 may include a voice-video assistant (VVA) 101, a conversation facilitation server 103, one or more user devices 105a . . . 105n, and one or more third-party servers 107, which connect with each other via a network 102. It is to be understood that, although FIG. 1 illustrates only one conversation facilitation server and one VVA for visual clarity, the conversation facilitation system 100 may include many conversation facilitation servers and VVAs that can be physically instantiated across various platforms.

The voice-video assistant (VVA) 101 includes hardware, software, and/or firmware for allowing a participant to join and conduct a conversation with other participants. In some embodiments, the VVA 101 may include a microphone 111, a speaker 113, a video camera 115, a video monitor 117, a computing subsystem 119, and a network interface 121. The VVA 101 receives, processes, and outputs audio data through the microphone 111 and the speaker 113. The VVA 101 may also use the optional video camera 115 and video monitor 117 to receive, process, and display video data. The video monitor 117 may be associated with a touchscreen and clickable button(s) to facilitate interactions with a user. The computing subsystem 119 of the VVA 101 includes other components, such as a processor, memory, storage, required for the VVA 101 to perform its function described herein. The network interface 121, which may also be part of the computing subsystem 119, communicates the VVA 101 to other entities of the conversation facilitation system 100 through a wire connection or a wireless connection.

As a networked device used by a participant to join and conduct a conversation, typically, the VVA 101 is a "smart speaker" such as the Amazon® Alexa, Google® Home, or Apple® Home Pod. In the scenario that the VVA 101 also handles video input and output, the example VVA devices with such video processing functionality may be the Amazon® Echo Show, Lenovo® Smart Display, and Harman® JBL Link View. Additionally the VVA 101 may be a smart computing device (e.g., smartphone) equipped with an appropriate software application for providing the functionality of allowing a participant to join and conduct a conversation with other participants.

The conversation facilitation server 103 includes hardware, software, and/or firmware that manage and facilitate an online conversation configured for a senior/user. In some embodiments, the conversation facilitation server 103 may track activities related to a senior/user, detect a trigger for a conversation, and set up the conversation for the senior/user. For example, if an amount of social interactions (e.g., a number of outgoing calls, minutes outside home) of a senior during a period of time is less than a threshold, the conversation facilitation server 103 may determine to set up an online conversation for the senior through the VVA 101 to mitigate loneliness of the senior. The conversation facilitation server 103 may also receive a conversation request for a conversation associated with a senior, e.g., from a doctor, and setup the conversation for the senior. Once the conversation is initiated, the conversation facilitation server 103 may monitor the progress of the conversation, and intervene when needed. For example, if no action is detected for a certain minute(s) during an ongoing conversation, the conversation facilitation server 103 may insert content related to the subject under discussion to remind participants of more content to talk. If the participant(s) gets too depressed in the conversation, the conversation facilitation server 103 may instruct the participant(s) to change to a different subject. The conversation facilitation server 103 may further conclude the conversation with a report, which highlights the conversation result based on certain metrics measured in the conversation and provides analysis for future improvement. The conversation facilitation server 103 will be described in detail below with reference to FIGS. 2A-2C.

The third-party server 107 includes one or more computing devices or systems for providing various computing functionalities, services, and/or resources to other entities included or not included in the conversation facilitation system 100. In some embodiments, the third-party server 107 hosts a network-based software application operable to provide computing functionalities, services and/or resources or functionalities, and to send data to and receive data from the other entities. For example, the third-party server 107 may be a search server that processes search information about web, video, news, maps, alerts, or an entertainment server that processes information about news, video, a personalized homepage, blogs, a reader, gadget subscriptions, or a social network server that processes social activity data including interactions through email, profile information, text messaging such as short message service (SMS), microblogs, geographical locations, comments on photos, a social graph and other social networking information, or other servers that process website ratings, reviews, etc.

In some embodiments, the third-party server 107 may incorporate with the conversation facilitation server 103 in managing a conversation, for example, detecting a trigger for a conversation associated with a senior/user, finding a subject of interest to participants of the conversation, etc. For example, if the third-party server 107 detects that a senior has been increasing the amount of time on watching videos in the past two weeks, the conversation facilitation server 103 may determine an active conversation with some people on the user's favorite video show may help improve the senior's health. In another example, when the conversation facilitation server 103 identifies the negative sentiment of a participant during an ongoing conversation, and the conversation facilitation server 103 may communicate with the third party server 107 to retrieve and select some jokes and add the jokes to the conversation to cheer the participant up.

The user devices 105a . . . 105n or collectively referred hereafter as user device 105 is a computing device including a processor, a memory, applications, a database, and network communication capabilities. For example, the user device 105 can be a laptop computer, a desktop computer, a tablet computer, a mobile telephone, a personal digital assistant (PDA), a mobile email device, a television with one or more processors embedded therein or coupled thereto or any other electronic device capable of accessing the network 102 and communicating with other entities of the conversation facilitation system 100.

The user device 105 receives and sends data to and from a support accessing the user device 105. The support may be a family member supporting a senior/user, a caregiver, a physician, and/or a doctor providing health service for the senior, or a friend of the senior, or even the senior himself/herself. For example, the user device 105 may receive a conversation request from a doctor, and communicate with the conversation facilitation server 103 to process the conversation request and return a conversation report to the doctor once the requested conversation has been conducted.

It should be noted the data collection described with reference to the VVA 101, the conversation facilitation server 103, the user device 105, and the third-party server 107 are performed subject to user consent. In some implementations, a user is prompted to explicitly allow data collection. Further, the user may opt in/out of participating in such data collection activities.

The network 102 includes hardware, software, and/or firmware that provide communications between the VVR 101, the conversation facilitation server 103, the user devices 105a . . . 105n, and the one or more third-party servers 107. In some embodiments, the network 102 may be a conventional type, wired and/or wireless, and may have numerous different configurations including a star configuration, token ring configuration, or other configurations. For instance, the network 102 may include one or more local area networks (LAN), wide area networks (WAN) (e.g., the Internet), satellite networks, telephone or cable networks, cellular networks, public networks, private networks, virtual networks, peer-to-peer networks, wireless networks implemented using a wireless protocol such as WiFi® or WiMax®, and/or any other interconnected data paths across which multiple devices may communicate. Although FIG. 1 illustrates a single block for the network 102, it should be understood that the network 102 may in practice comprises any number of combinations of networks, as noted above.

Figure 2A:
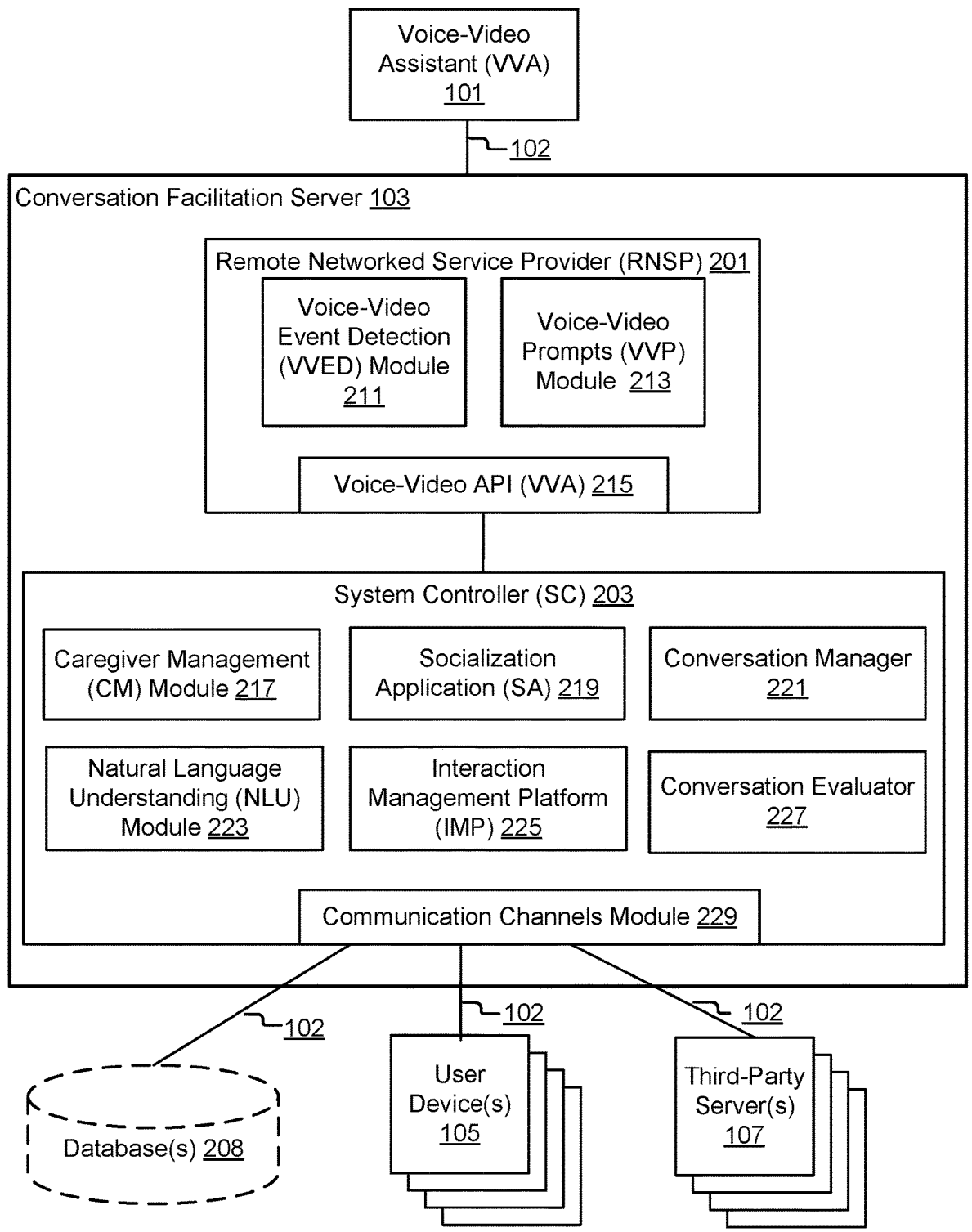
FIG. 2A is a block diagram of an example conversation facilitation system including various components of an example conversation facilitation server.

FIG. 2A is a block diagram of an example conversation facilitation system 100 including various components of an example conversation facilitation server 103. As illustrated in the figure, the conversation facilitation server 103, which includes a remote networked service provider (RNSP) 201 and a system controller (SC) 203, connects with the VVA 101, the user device 105, the third party server 107 and database(s) 208 via the network 102.

The conversation facilitation server 103 connects with the VVA 101 through the RNSP 201 over the network 102. The RNSP 201 includes hardware, software, and/or firmware for processing audio and video data captured by the VVA 101 and converting the data to streams of time-stamped text. As depicted in FIG. 2A, the RNSP 201 may include a voice-video event detection (VVED) module 211, a voice-video prompts (VVP) module 213, and voice-video API (VVA) 215.

The VVED module 211 includes hardware, software, and/or firmware for applying recognition on raw audio and video data received from the VVA 101 and outputting a recognition result. The audio data is associated with an audio event, for example, a spoken instruction such as "Care system, call my new friend Jane" or "Care system, schedule a conversation with my bridge group tomorrow morning." The video data is associated with a video event, for example, a face, a facial expression, a number of people in view and their distance from the camera 113, a gesture (e.g., a sign language), etc.

In some embodiments, the VVED module 211 may perform pattern matching when implementing voice-video recognition algorithm(s) to recognize audio and video data. For example, the VVED module 211 may determine different interpretations/voice patterns for different users based on analysis on varying speed of speech delivery, and recognize an originator of a voice based on the different interpretations/voice patterns. Additionally the VVED module 211 may recognize voice from both the microphone 111 and the speaker 115 of the VVA 101. For example, the VVED module 211 may perform speaker recognition to identify which user has spoken which phrase. In some embodiments, the VVED module 221 may also perform voice stress analysis to the audio stream from the microphone.

In some embodiments, the VVED module 211 may apply recognition on audio and video data (e.g., related to a conversation) to determine who was present, a role of that person (e.g., senior, caregiver, family member, or other), what was said, and an identifier for an audio or video event that was detected (e.g., the audio event was a speech event), timestamp each audio and/or video event, and generate timestamped text based on the recognized data. For example, the VVED module 211 may recognize the audio stream of a conversation and generate text including "Caregiver Martha said "Good morning Mary, did you sleep well last night?" at 8:05 AM on Fri. Oct. 5, 2018," or "Patient Mary said "Hi Martha. It's good to see you again. Yes, I slept straight through for eight hours." at 8:06 AM on Fri. Oct. 5, 2018."

In some embodiments, the VVED module 211 may transmit the time-stamped text, speaker recognition result(s), audio and video events, as well as the raw audio and video data captured by the VVA 101 (i.e., a recognition result) to the SC 203 through the VVA 215. Altogether, this information is also referred hereafter as a dialog act.

The VVP module 213 includes hardware, software, and/or firmware for generating a VVA prompt for interacting with a user through the VVA 101. For example, the VVP module 213 may send an instruction to a senior or ask the senior a question or remind the senior of something to do using a VVA prompt. In some embodiments, the VVP module 213 may be included in the SC 203, and the SC 203 may send the VVA prompt and instruction to the RNSP and VVA 101.

A VVA prompt is a tuple comprised of a VVA address, a modality, content, rendering parameter(s). An example voice VVA tuple is (128875, TEXT_TO_SPEECH, "Mary, can you tell us about the first movie you ever saw?", Voice_Type: soft female, Volume: medium, Intonation: soothing), where 128875 identifies a specific VVA, including its IP address. An example video VVA tuple is (128875, TEXT_TO_AVATAR, "Mary would you like to have a chat with others?", Avatar ID: patient Nurse Jane, Expression: cheerful, Volume: medium, Intonation: friendly inquisitive). The TEXT_TO_AVATAR modality signals that the VVP module 213 to look up Avatar ID (patient Nurse Jane) in the database 208. The VVA prompt also shows that the user with Avatar ID "patient Nurse Jane" speaks the indicated phrase with a cheerful expression, at medium volume, and in a friendly as well as inquisitive tone.

The VVA 215 is an interface that serves as an intermediary for communication between RNSP 201 and SC 203.

The SC 203, as illustrated in FIG. 2A, may include a caregiver management (CM) module 217, a socialization application (SA) 219, a conversation manager 221, a natural language understanding (NLU) module 223, an interaction management platform (IMP) 225, a conversation evaluator 227, and a communication channels module 229, which will be described in detail with reference to FIGS. 2B and 2C.

Figure 2B:
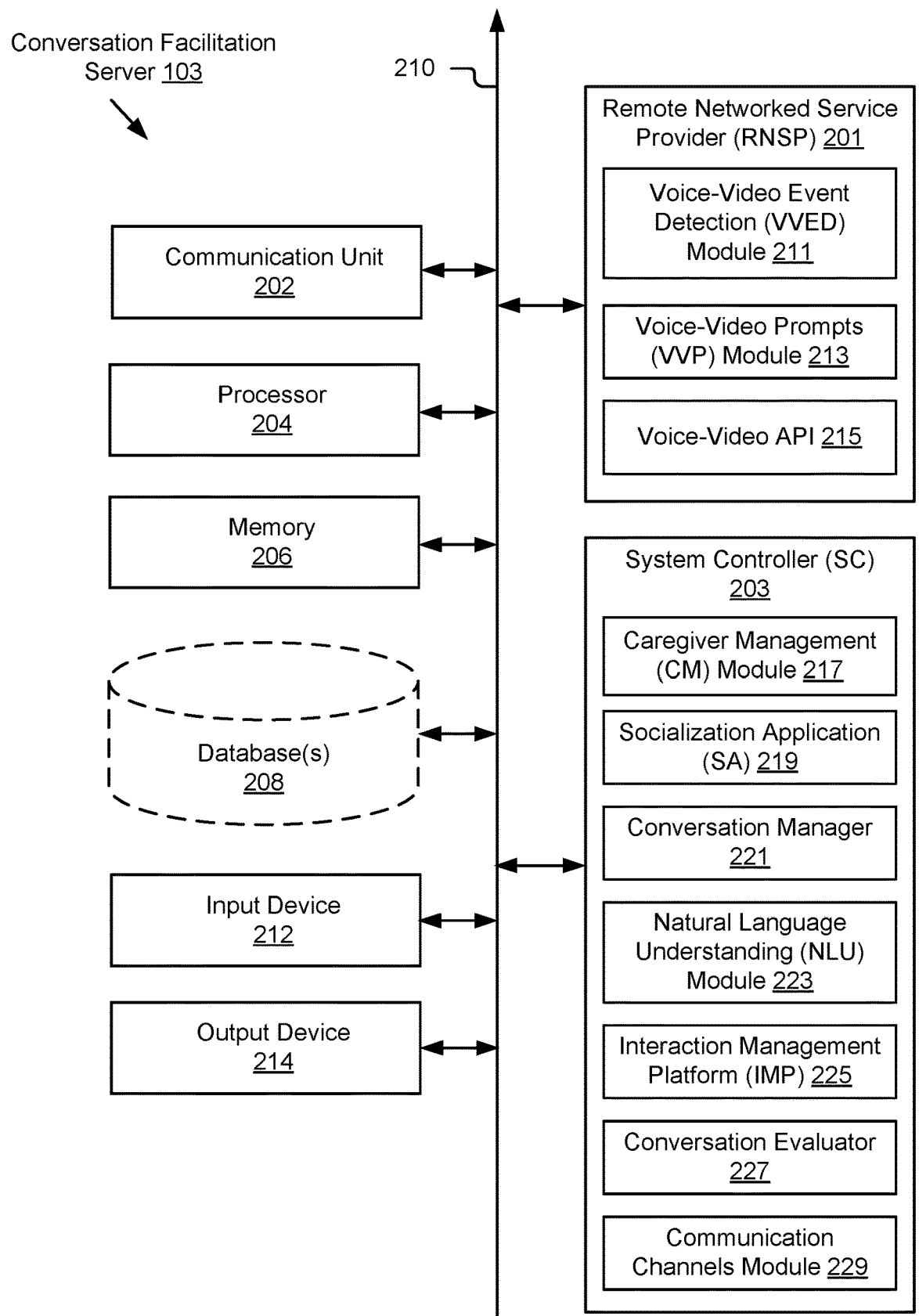
FIG. 2B is a block diagram of an example conversation facilitation server.

Referring now to FIG. 2B, which illustrates an example conversation facilitation server 103. As depicted, the conversation facilitation server 103 may include a communication unit 202, a processor 204, a memory 206, database(s) 208, an input device 212, an output device 214, a remote networked service provider (RNSP) 201, and a system controller (SC) 203, which may be communicatively coupled by a communication bus 210. The conversation facilitation server 103 depicted in FIG. 2B is provided by way of example and it should be understood that it may take other forms and include additional or fewer components without departing from the scope of the present disclosure. For instance, various components of the computing device may be coupled for communication using a variety of communication protocols and/or technologies including, for instance, communication buses, software communication mechanisms, computer networks, etc. While not shown, the conversation facilitation server 103 may include various operating systems, sensors, additional processors, and other physical configurations. The communication unit 202, processor 204, memory 206, etc., are representative of one or more of these components.

The communication unit 202 may include one or more interface devices (I/F) for wired and wireless connectivity among the components of the conversation facilitation system 100. For instance, the communication unit 202 may include, but is not limited to, various types known connectivity and interface options. The communication unit 202 may be coupled to the other components of conversation facilitation server 103 via the bus 210. The communication unit 202 can provide other connections to the network 102 and to other entities of the conversation facilitation system 100 using various standard communication protocols.

In some embodiments, the communication unit 202 includes a wireless transceiver for exchanging data with the conversation facilitation server 103, the VVA 101, the one or more user devices 105, the one or more third-party servers 107, or any other communication channel using one or more wireless communication methods, such as IEEE 802.11, IEEE 802.16, BLUETOOTH® or another suitable wireless communication method.

In some embodiments, the communication unit 202 includes a cellular communications transceiver for sending and receiving data over a cellular communications network such as via short messaging service (SMS), multimedia messaging service (MMS), hypertext transfer protocol (HTTP), direct data connection, WAP, e-mail or another suitable type of electronic communication. In some embodiments, the communication unit 202 includes a wired port and a wireless transceiver. The communication unit 202 also provides other conventional connections to the network for distribution of files and/or media objects using standard network protocols such as TCP/IP, HTTP, HTTPS and SMTP as will be understood to those skilled in the art.

The processor 204 comprises an arithmetic logic unit, a microprocessor, a general purpose controller or some other processor array to perform computations and provide electronic display signals to a display device. The processor 204 may be coupled to the bus 210 for communication with the other components. The processor 204 processes data signals and may comprise various computing architectures including a complex instruction set computer (CISC) architecture, a reduced instruction set computer (RISC) architecture, or an architecture implementing a combination of instruction sets. Although only a single processor is shown in FIG. 2B, multiple processors may be included. The processing capability might be enough to perform complex tasks, including various types of feature extraction and matching. It will be obvious to one skilled in the art that other processors, operating systems, sensors, displays and physical configurations are possible.

The memory 206 stores instructions and/or data that may be executed by processor 204. The memory 206 is coupled to the bus 210 for communication with the other components. The instructions and/or data may comprise code for performing any and/or all of the techniques described herein. The memory 206 may be a dynamic random access memory (DRAM) device, a static random access memory (SRAM) device, flash memory or some other memory device known in the art. In some embodiments, the memory 206 also includes a non-volatile memory or similar permanent storage device and media such as a hard disk drive, a floppy disk drive, a CD ROM device, a DVD ROM device, a DVD RAM device, a DVD RW device, a flash memory device, or some other mass storage device known in the art for storing information on a more permanent basis.

The database(s) 208 may include information sources for storing and providing access to data. In some implementations, database(s) 208 may store data associated with a database management system (DBMS) operable on the conversation facilitation system 100. For example, the DBMS could include a structured query language (SQL) DBMS, a NoSQL DMBS, various combinations thereof, etc. In some instances, the DBMS may store data in multi-dimensional tables comprised of rows and columns, and manipulate, (e.g., insert, query, update and/or delete), rows of data using programmatic operations.

The database(s) 208 may be included in the conversation facilitation server 103 or in another computing system and/or storage system distinct from but coupled to or accessible by conversation facilitation server 103. The database(s) 208 can include one or more non-transitory computer-readable mediums for storing the data. In some implementations, the database(s) 208 may be incorporated with the memory 206 or may be distinct therefrom.

The input device 212 may include any device for inputting information into the conversation facilitation server 103. In some embodiments, the input device 212 may include one or more peripheral devices. For example, the input device 212 may include a keyboard, a pointing device, microphone, an image/video capture device (e.g., camera), a touch-screen display integrated with the output device 214, etc. The output device 214 may be any device capable of outputting information from the conversation facilitation server 103. The output device 214 may include one or more of a display (LCD, OLED, etc.), a printer, a haptic device, an audio reproduction device, a touch-screen display, a remote computing device, etc. In some implementations, the output device is a display which may display electronic images and data output by a processor of the conversation facilitation server 103 for presentation to a user, such as the processor 204 or another dedicated processor.

The bus 210 can include a communication bus for transferring data between components of a computing device or between computing devices, a network bus system including the network 102 or portions thereof, a processor mesh, a combination thereof, etc. The software communication mechanism can include and/or facilitate, for example, inter-method communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication could be secure (e.g., SSH, HTTPS, etc.).

The components 201, 202, 203, 206, 208, 212, and/or 214 may be communicatively coupled by bus 210 and/or processor 204 to one another and/or the other components of the conversation facilitation server 103. In some implementations, the components 201, 202, 203, 206, 208, 212, and/or 214 may include computer logic (e.g., software logic, hardware logic, etc.) executable by the processor 204 to provide their acts and/or functionality. In any of the foregoing implementations, these components 201, 202, 203, 206, 208, 212, and/or 214 may be adapted for cooperation and communication with processor 204 and the other components of the conversation facilitation server 103.

Figure 2C:
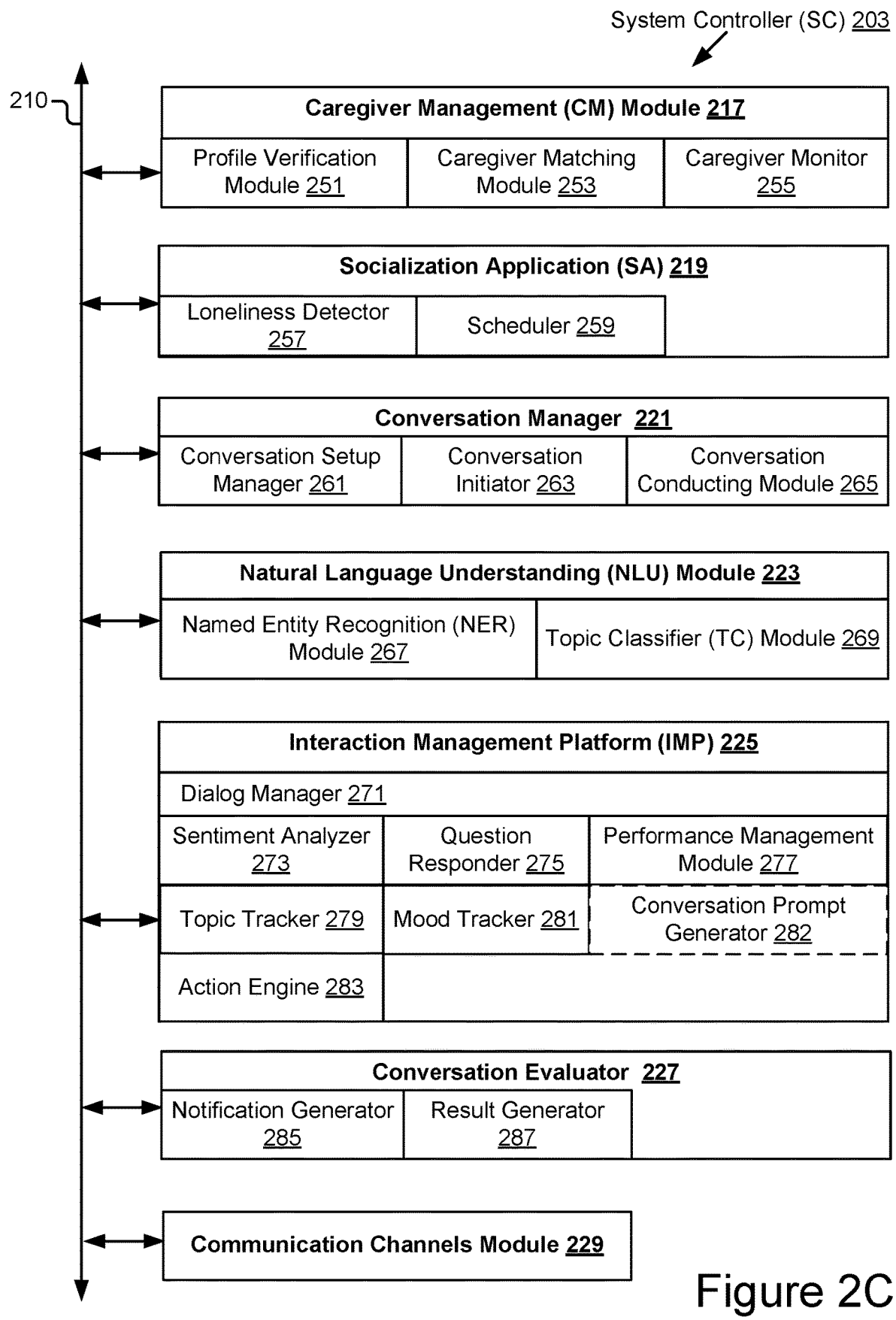
FIG. 2C is a block diagram of an example system controller.

Referring now to FIG. 2C, which provides further details relating to the system controller (SC) 203 that includes a caregiver management (CM) module 217, a socialization application (SA) 219, a conversation manager 221, a natural language understanding (NLU) module 223, an interaction management platform (IMP) 225, a conversation evaluator 227, and a communication channels module 229. The communication channels module 229 allows the components of the SC 203 to communicate with each other internally and/or to communicate externally with other components of the conversation facilitation system 100. The components 217-227 included in the SC 203 will be described in detail below.

The caregiver management (CM) module 217 includes hardware, software, and/or firmware for implementing caregiver management including training, supervising caregivers, monitoring their performance of in-house healthcare, etc. As illustrated in FIG. 2C, the caregiver management (CM) module 217 may include a profile verification module 251, a caregiver matching module 253, and a caregiver monitor 255.

The profile verification module 251 includes hardware, software, and/or firmware that verifies a caregiver's profile. A caregiver is a healthcare provider that specifically provides in-house healthcare for clients. The caregiver's profile includes the caregiver's demographic information, experience areas, achieved certificates, etc. In some embodiments, the profile verification module 251 may examine and verify the information (e.g., based on communication with other servers) included in the profile when storing the profile in the database 208 at the first time, when updating the profile information stored in the database 208, when retrieving and transmitting the profile to a module/device.

The caregiver matching module 253 includes hardware, software, and/or firmware that recommends a caregiver for a senior/user. In some embodiments, responsive to receiving a caregiver request for a senior/user, the caregiver matching module 253 may compare parameter(s) specified in the request to caregiver information stored in the database 208, and search for a matched caregiver. The parameters, e.g., expertise, work hours, gender, etc., may be manually specified by the requestor (e.g., the senior/user, a professional care manager, a doctor) and/or automatically specified by the caregiver matching module 253. For example, the caregiver matching module 253 may automatically add certain restraint(s) when searching for a caregiver for a senior that meets certain condition(s) such as over 80 years old, diabetic, etc.

The caregiver monitor 255 includes hardware, software, and/or firmware that monitors activities related to healthcare service provided by a caregiver. In some embodiments, the caregiver monitor 255 may allow a caregiver to sign up for shifts, and track the times when the caregiver arrives and departs for the shifts. The caregiver monitor 255 may also record every interaction between the caregiver and the senior/user and the schedule of the caregiver, and store the recorded data in the database(s) 208.

The socialization application (SA) 219 includes hardware, software, and/or firmware that determine and schedule an online conversation for a senior/user to mitigate loneliness. As illustrated in FIG. 2C, the socialization application (SA) 219 may include a loneliness detector 257 and a scheduler 259.

The loneliness detector 257 includes hardware, software, and/or firmware that track and measure loneliness for a senior/user. In some embodiments, the loneliness detector 257 may compute a quantitative loneliness score to measure the loneliness of a senior/user based on loneliness test(s) related to specific features. These features may include minutes speaking to a caregiver, minutes speaking to another person, minutes speaking on the phone, minutes speaking to oneself, minutes in the home, minutes outside the home, minutes on incoming calls, minutes on outgoing calls, minutes having a visitor in the home, minutes having a caregiver in the home, minutes of smartphone usage, minutes of personal computing device usage, characters typed per minute (associated with typing event(s) on the smartphone and/or personal computing device), a number of steps (associated with step event(s) generated by the smart phone or other smart computing device(s) including a smart watch), a number of motion events (generated by smart computing device(s) including a smart motion sensor), an average movement speed (e.g., how fast a senior moves from her bed to bathroom at a certain time), a number of audio event (e.g., how many times a "dishes dropped" event or a "silverware dropped" event occurred in the last two days), etc. The loneliness detector 257 may calculate the occurrence of a given feature over a given interval, analyze these numeric features by a machine learning algorithm, and determine a loneliness score for a user.

The loneliness detector 257 may signal the scheduler 259 that a loneliness score has been determined for a senior/user. In some embodiments, the loneliness detector 257 transmits the loneliness score to the scheduler 259 to determine whether a conversation for the senior/user needs to be scheduled. In other embodiments, the loneliness detector 257 determines that a loneliness score reaches an alert level (e.g., exceeding a predefined threshold) and signals the scheduler 259 to schedule a conversation for the senior/user.

The scheduler 259 includes hardware, software, and/or firmware for requesting and/or scheduling a conversation based on a conversation request. In some embodiments, the scheduler 259 may detect a trigger for a conversation and generate a conversation request for the conversation. For example, the scheduler 259 receives, from the loneliness detector 257, a signal that the loneliness score of a senior is lower than a predefined threshold, and generates a conversation request for the senior such that the senior can talk with other person(s) on a topic of interest instead of being alone. In other embodiments, the scheduler 259 may receive a conversation request from a user. The conversation may be a voice-video call established with VVA(s) 101 associated with the participants.

The conversation request may be a request for a proactive conversation or a request for a reactive conversation. Both types of conversation are initiated for purpose of mitigating loneliness of a senior. From the foregoing the proactive conversation may be automatically requested for the senior by the scheduler 259, or it may be requested by a family caregiver, a professional care manager, a physician or other support of the senior. The reactive conversation is requested by the senior herself/himself. In some embodiments, the scheduler 259 may communicate with the conversation manager 221 (as described below) to schedule, initiate and/or execute a proactive conversation and a reactive conversation.

Figure 3:
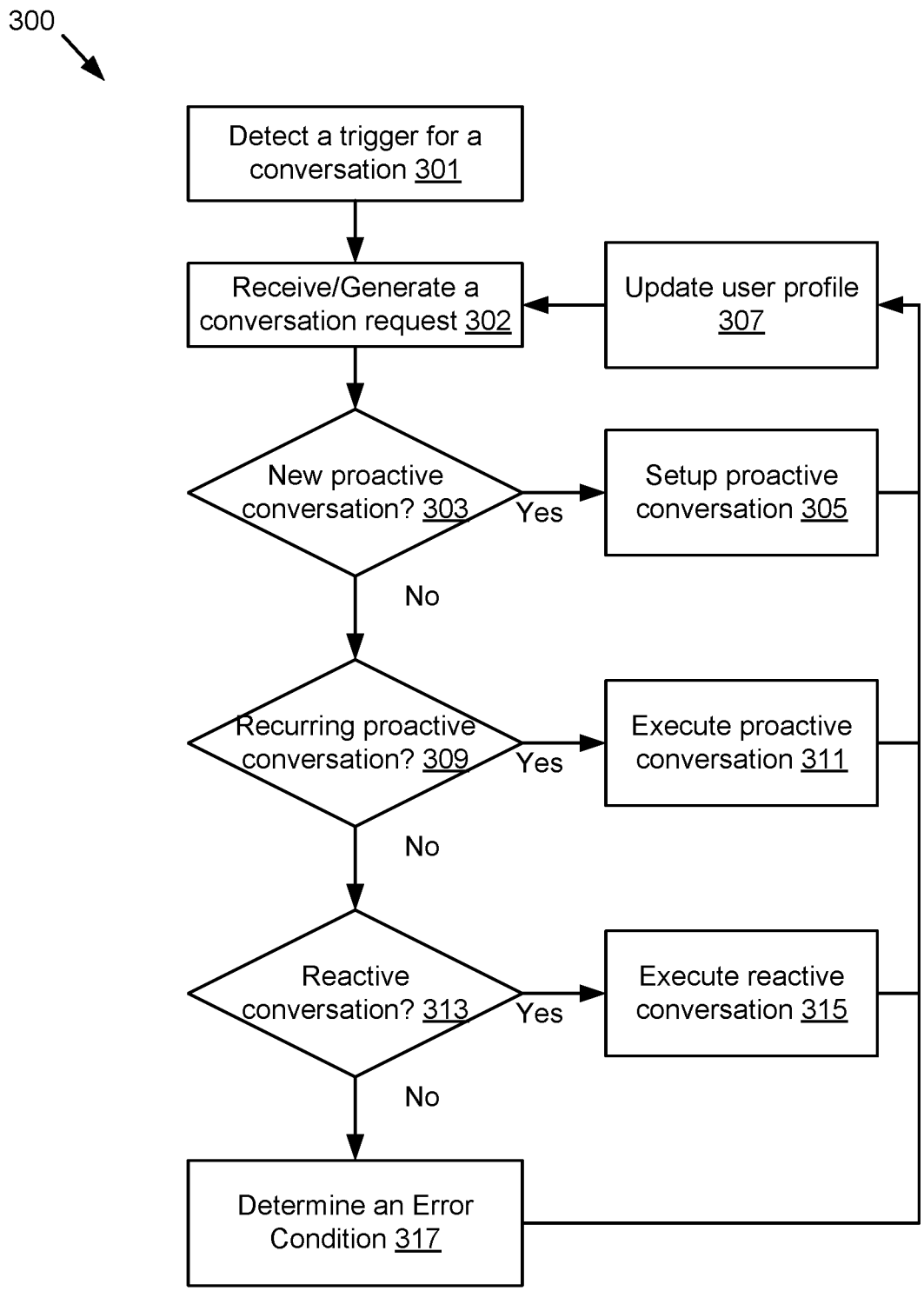
FIG. 3 is a flowchart of an example method for handling a conversation request for an online conversation associated with a senior.

FIG. 3 is a flowchart of an example method 300 for handling a conversation request for an online conversation associated with a senior. At step 301, the scheduler 259 detects a trigger for a conversation, for example, the loneliness score of a senior being lower than a specific threshold. At step 302, the scheduler 259 generates/receives a conversation request. The scheduler 259 may automatically generate a conversation request for a conversation associated with a senior in response to detecting a trigger for the conversation, or receive a conversation request for the conversation from the senior or a requestor other than the senior. At step 303, the scheduler 259 determines whether the conversation request is for a new proactive conversation. If the request is for a new proactive conversation, at step 305, the scheduler 259 may communicate with a conversation setup manager 261 included in the conversation manager 221 (as described below) to set up the new proactive conversation. Once the new proactive conversation has been set up, at step 307, the scheduler 259 may also update the user profile of the senior with the information of the new proactive conversation. In some embodiments, the scheduler 259 may interact with the conservation manager 221 to receive and associate a conversation object of the new proactive conversation to the user profile of the senior, and/or include the conversation object in the user profile. Example conversation objects are shown in FIGS. 5 and 6.

If the request is not for a new proactive conversation, at step 309, the scheduler 259 determines whether the request is for a recurring proactive conversation that has previously been scheduled for a specified time. If the request is for a recurring proactive conversation, at step 311, the scheduler 259 may communicate with a conversation initiator 263 and a conversation conducting module 265 included in the conversation manager 221 to initiate and execute the recurring proactive conversation at the specified time. Otherwise, at step 313, the scheduler 259 determines whether the request is for a reactive conversation. If yes, at step 315, the scheduler 259 may also communicate with the conversation initiator 263 and the conversation conducting module 265 to initiate and execute the reactive conversation. In addition, the execution of the conversations at steps 311 and 315 may also result in updating the user profile at step 307, e.g., with an updated conversation object of the conversation.

However, if the scheduler 259 determines, at step 313, that the request is also not for a reactive conversation, the scheduler 259 may specify an error condition at step 317 and update the user profile with the error condition indicating that no valid request for a proactive or reactive conversation is received and processed at step 307.

Referring back to FIG. 2C, the conversation manager 221 includes hardware, software, and/or firmware for setting up and managing a conversation. As illustrated in FIG. 2C, the conversation manager 221 may include a conversation setup manager 261, a conversation initiator 263, and a conversation conducting module 265.

Figure 4:
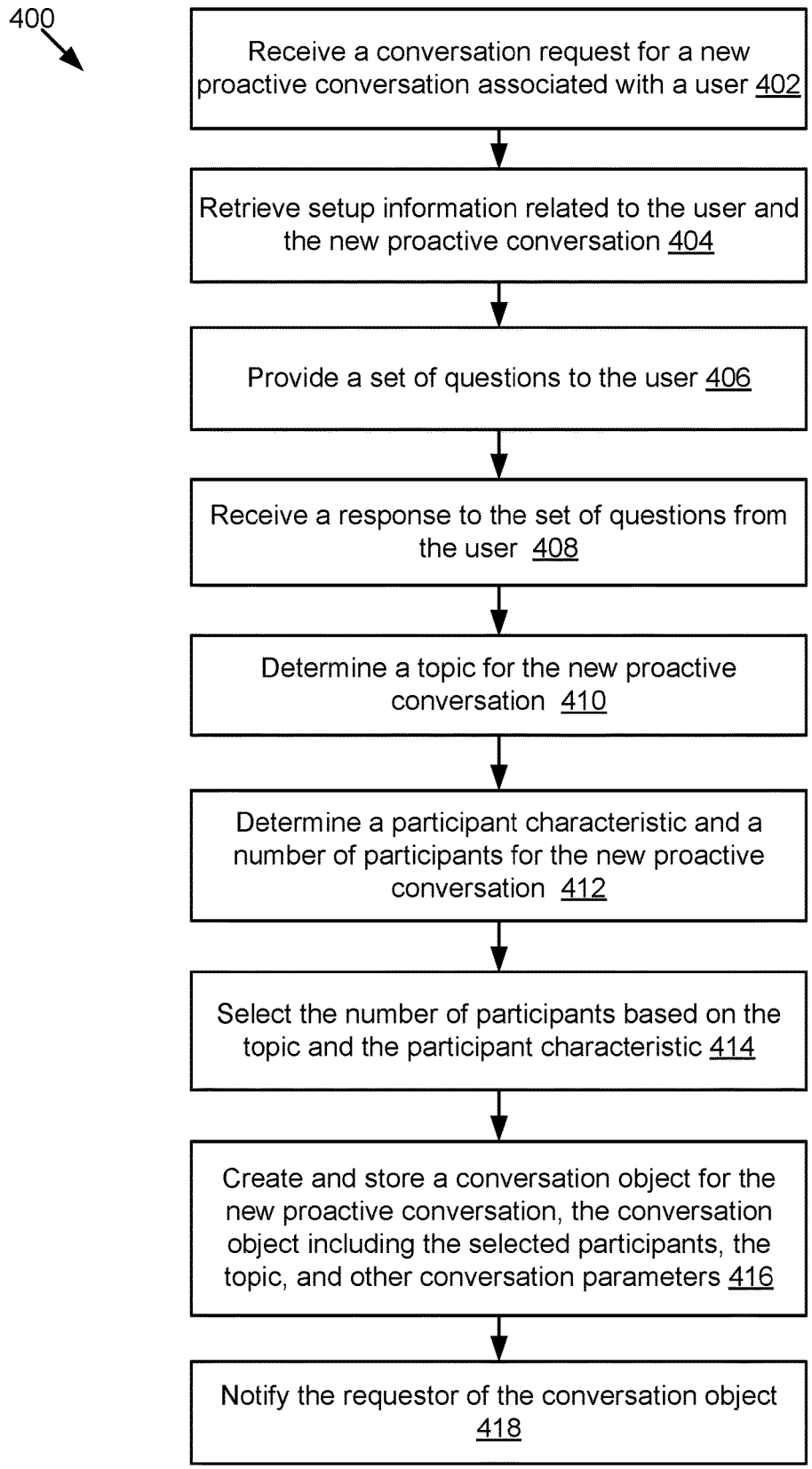
FIG. 4 is a flowchart of an example method for setting up a proactive conversation.

The conversation setup manager 261 includes hardware, software, and/or firmware that set up or schedule a new proactive/reactive conversation for a senior/user. An example method 400 for the conversation setup manager 261 in communication with other components of the SC 203 to set up a new proactive conversation is illustrated in FIG. 4. The process for setting up or scheduling a reactive conversation is similar to the process shown in FIG. 4 and therefore will not be described herein.

At step 402 of FIG. 4, the conversation setup manager 261 receives a conversation request for a new proactive conversation associated with a user/senior from the scheduler 259. The request may be generated by a requestor such as a family caregiver, a professional care manager, a physician, or other support for the senior. Or the scheduler 259 may incorporate with the loneliness detector 257 to detect a trigger for a conversation and automatically generate a new proactive conversation request.

Responsive to receiving the conversation request, the conversation setup manager 261 triggers the set-up process for a new proactive conversation, for example, scheduling a setup call with the senior to collect information and get the conversation ready for a specified time as described in steps 404-418. At step 404, the conversation setup manager 261 retrieves setup information related to the user and the new proactive conversation. For example, the conversation setup manager 261 may retrieve a setup proactive conversation object from the database 208. A conversation object, as shown in FIGS. 5 and 6, stores data related to setting up, initiating, or conducting a conversation. In some embodiments, the conversation setup manager 261 may use a template to generate the setup proactive conversation object based on the request for the new proactive conversation, and the conversation setup manager 261 as well as other components of the SC 203 may update the setup proactive conversation object as the corresponding conversation is scheduled, initiated, and/or conducted. In some embodiments, the conversation setup manager 261 may associate a conversation object of a conversation to a senior/user and store the conversation object in the database(s) 208. For example, the conversation setup manager 261 may store the conversation object in the user profile of the senior/user.

At step 406, the conversation setup manager 261 determines a set of questions from the retrieved information including the setup proactive conversation object and provides the set of questions to the user. At step 408, the conversation setup manager 261 receives a response to the set of questions from the user. Based on the response, the conversation setup manager 261 determines a topic for the new proactive conversation at step 410, and determines a participant characteristic and a number of participants for the new proactive conversation at step 412. In some embodiments, the response may include a confirmation that the senior agrees to participate the conversation, a preferred topic, a desired familiarity of the other participants with the topic, and other characteristics of the participants such as age and gender.

At step 414, the conversation setup manager 261 selects the number of participants based on the topic and the participant characteristic. In some embodiments, the conversation setup module 261 may compute a compatibility score for each candidate participants using a compatibility function based on the topic and the characteristic, and select the number of participants based on the compatibility score. For example, if the number of participants is N=5, the conversation setup manager 261 may retrieve information of M=2*N=10 candidate participants with the specified characteristic(s) from the database 208, compute a compatibility score for each of 10 candidate participants, and select the candidate participants with top five compatibility scores as the participants of the conversation. In some embodiments, the conversation setup manager 261 may rank the candidate participants in order of participant characteristic (e.g., experience with the topic), from most to least, and contact them in order, one by one. The conversation setup manager 261 may stop contacting the candidate participants and obtain a list of participants when the first N people agree to participate in the proposed proactive conversation at the specified time.

Next at step 416, the conversation setup manager 261 creates and stores a conversation object for the new proactive conversation, the conversation object including the selected participants, the topic, and other conversation parameters (e.g., time, duration, recurrence frequency, etc.). In some embodiments, the conversation setup manager 216 may update the setup conversation object to create the conversation object associated with the conversation. Once the conversation object is created, at step 418, the conversation setup manager 261 notifies the requestor of the conversation object indicating that the conversation has been scheduled.

FIG. 5 illustrates an example setup proactive conversation object 500. The object identifies a senior/user, a start date for a setup call, a duration of the setup call, a time when the proactive conversation is expected to start, a prescribed recurrence frequency for the proactive conversation, a prescribed duration of each conversation, a name of the requestor, a position of the requestor, requirement for the participants in the conversation, a set of questions that help design the conversation, and a format of a conversation result.

As shown in the example object 500, the conversation setup manager 261 may initiate a setup call using the VVA 101 associated with senior Mary Smith and interact with her at 11:00 AM on Sep. 2, 2018 for ten minutes. Dr. Patty, who is a physician, has requested recurring proactive conversations for Mary Smith by prescribing 30 minute conversations every weekday for the next six months starting on Sep. 3, 2018 at 1:05 PM. During the setup call, the conversation setup manager 261 may present a set of questions to Mary Smith, and determine a topic, a number of participants, experience of the participants with the topic, and characteristic(s) of the participants from Mary Smith's response. The conversation setup manager 261 may then select the number of the participants in the conversation based on the topic, experience of the participants with the topic, and characteristic(s) of the participants.

The set of questions from the conversation object is also designed to help structure subsequent conversation(s). The example questions for Mary Smith shown in FIG. 5 include:
Would you like to chat with others?
How many people would you like to talk with?
What topics would you like to discuss? We can help find people who know about soap operas, movies, football, tennis, baseball, knitting, bridge, soccer, local news, politics, etc.
How many years familiarity should the participants have with the topic?
What should be age and gender of participants? [female, male, both]

In the example of FIG. 5, Mary Smith confirms that she would like to talk with three other seniors about the soap opera Young and Restless. These three other seniors should have watched this soap opera for at least 20 years, and they should be of any age and any gender. Responsive to receiving this response, the conversation setup manager 261 may retrieve information of M=2*N=6 candidate participants with the specified characteristic(s) from the database 208, and contact these six people in the order from the highest ranking to lowest ranking on experience with the topic until finding three people agreeing to participate in the proposed proactive conversation at the specified time. Once the participants are determined, the conversation setup manager 261 may update the setup conversation object and store the updated conversation object for the conversation in the database 208. The conversation setup manager 261 may further notify the requestor Dr. Patty that a conversation for Mary Smith has been successfully scheduled, as well as the information of participants (e.g., name, age, gender, and experience with the topic).

FIG. 6 illustrates an example of a proactive conversation object 600, which is updated with information received from the setup procedure described in FIG. 5. The updated information related to the scheduled proactive conversation for Mary Smith may include names of other participants, topic, time, duration, recurrence frequency, etc. For example, the updated conversation object 600 indicates that Mary Smith's next scheduled conversation about the topic "soap opera" will occur on Sep. 3, 2018 at 1:05 PM for 30 minutes. This is part of a series that occurs daily Monday through Friday. Other participants include Joan Jones, Edwina Edwards, and Mike Mellow. Questions to prime the discussion include "What do you think character X will do next?" "Where did character X go?" "Who is Victoria's real father?"

The updated conversation object 600 in FIG. 6 may also include sources for external information that could help generate more questions or answer open questions, and specify that a result of the conversation reported to the requestor Dr. Patty should include a length of the conversation, names of participants, a percentage of time the senior Mary Smith has participated, the tone of the conversation, and the response of Mary Smith to jokes, etc. Further, the proactive conversation object 600 may store the external contacts related to the conversation. This includes people among the participants that were contacted separately by Mary Smith, the date of each contact, the duration of each contact, etc. It should be noted that information of the object 600 may be updated by different components of the SC 203 as the conversation progresses.

In addition to the conversation setup manager 261, the conversation manager 221 as depicted in FIG. 2C further includes a conversation initiator 263 and a conversation conducting module 265. The conversation initiator 263 includes hardware, software, and/or firmware for initiating a conversation that has been scheduled and set up by the conversation setup manager 261. The conversation conducting module 265 includes hardware, software, and/or firmware for enabling a conversation to be smoothly implemented among a group of participants.

Figure 7:
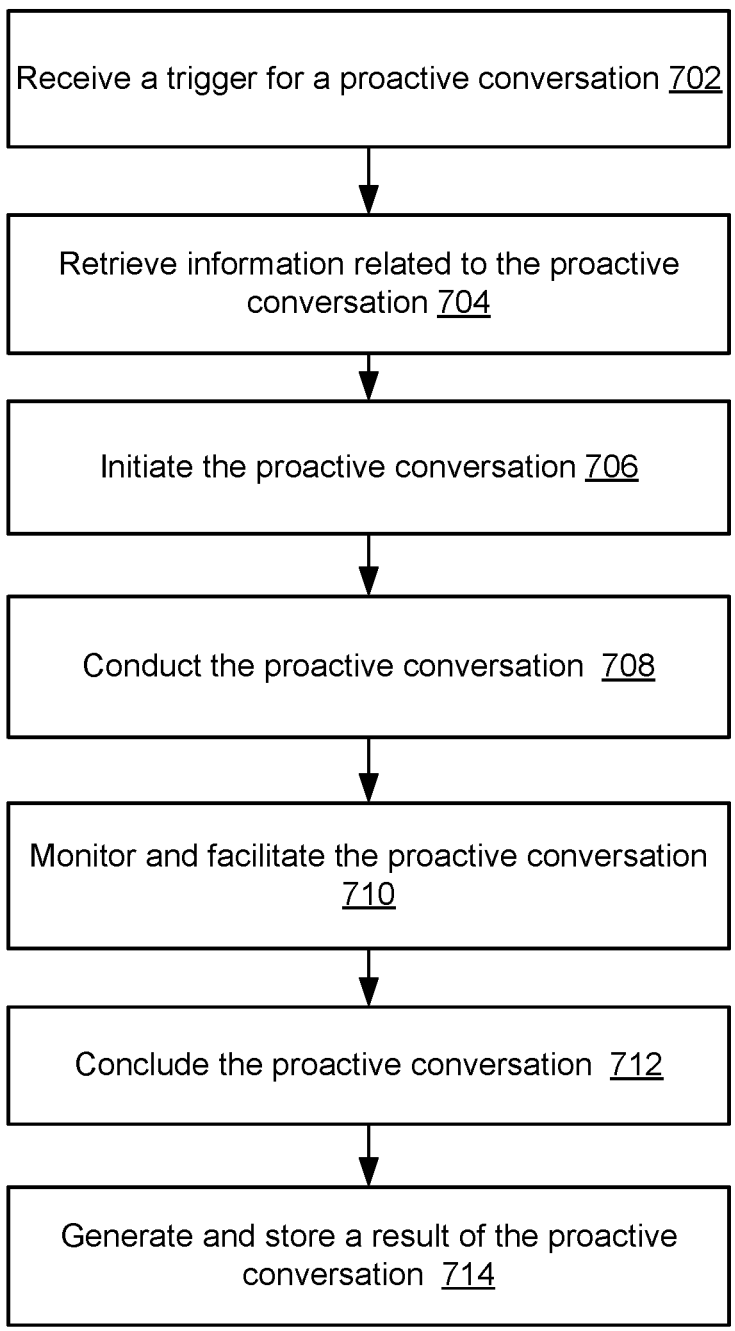
FIG. 7 is a flowchart of an example method for executing a proactive conversation.

FIG. 7 illustrates a flowchart of an example method 700 for executing a proactive conversation by the conversation manager 221 in combination with other components of the conversation facilitation system 100. As illustrated in the figure, at step 702, the scheduler 259 receives a trigger for a proactive conversation. For example, the scheduler 259 receives a signal that a senior has been staying home for over a threshold amount of time, and generates a conversation request to trigger a proactive conversation. Or the scheduler 259 receives a prescription of a conversation for a senior, e.g., a conversation request, from a doctor and triggers a proactive conversation. The scheduler 259 passes the conversation request to the conversation setup manager 261 for setting up the proactive conversation. At step 704, the conversation setup manager 261 retrieves information related to the proactive conversation, for example, a setup proactive conversation object, and uses the information to set up the proactive conversation and create/update a conversation object for the proactive conversation.

Once the proactive conversation is set up and when a scheduled time for the conversation arrives, this conversation can be initiated, conducted, and concluded as described in steps 706-714. At step 706, the conversation initiator 263 initiates the proactive conversation at step 706, the conversation conducting module 265 conducts the proactive conversation at step 708, an interaction management platform (IMP) 225 as described below monitors and facilitates the proactive conversation at step 710. Responsive to detecting an end of the conversation, a conversation evaluator 227 as described below concludes the proactive conversation at step 712, and generates and stores a result of the proactive conversation at step 714. These steps 706-714 will be described in detail in FIGS. 8A-8C and subsequent figures.

Figure 8A:
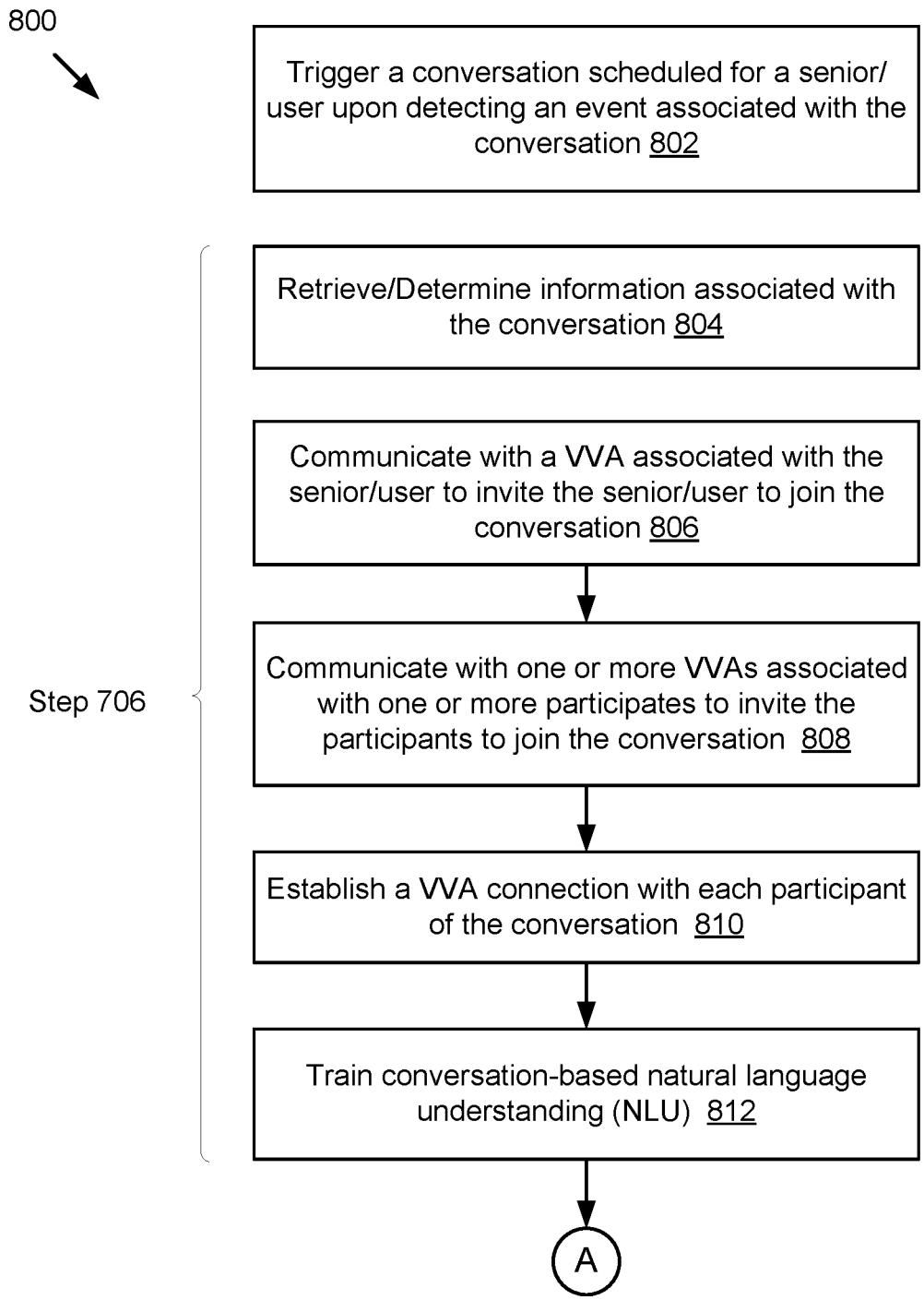
FIGS. 8A-8C are a flowchart of another example method for executing a proactive conversation.
Figure 8B:
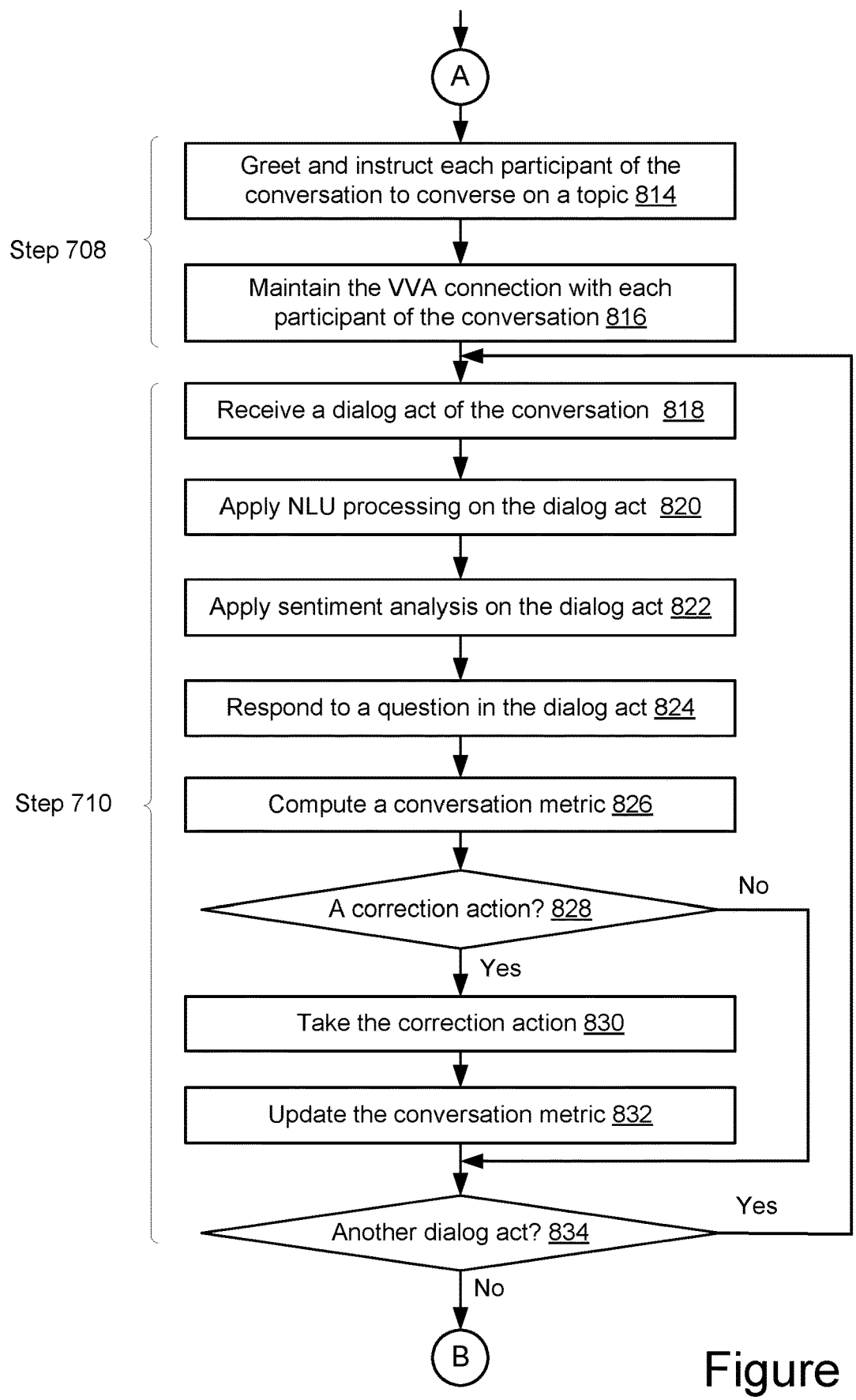
Figure 8C:
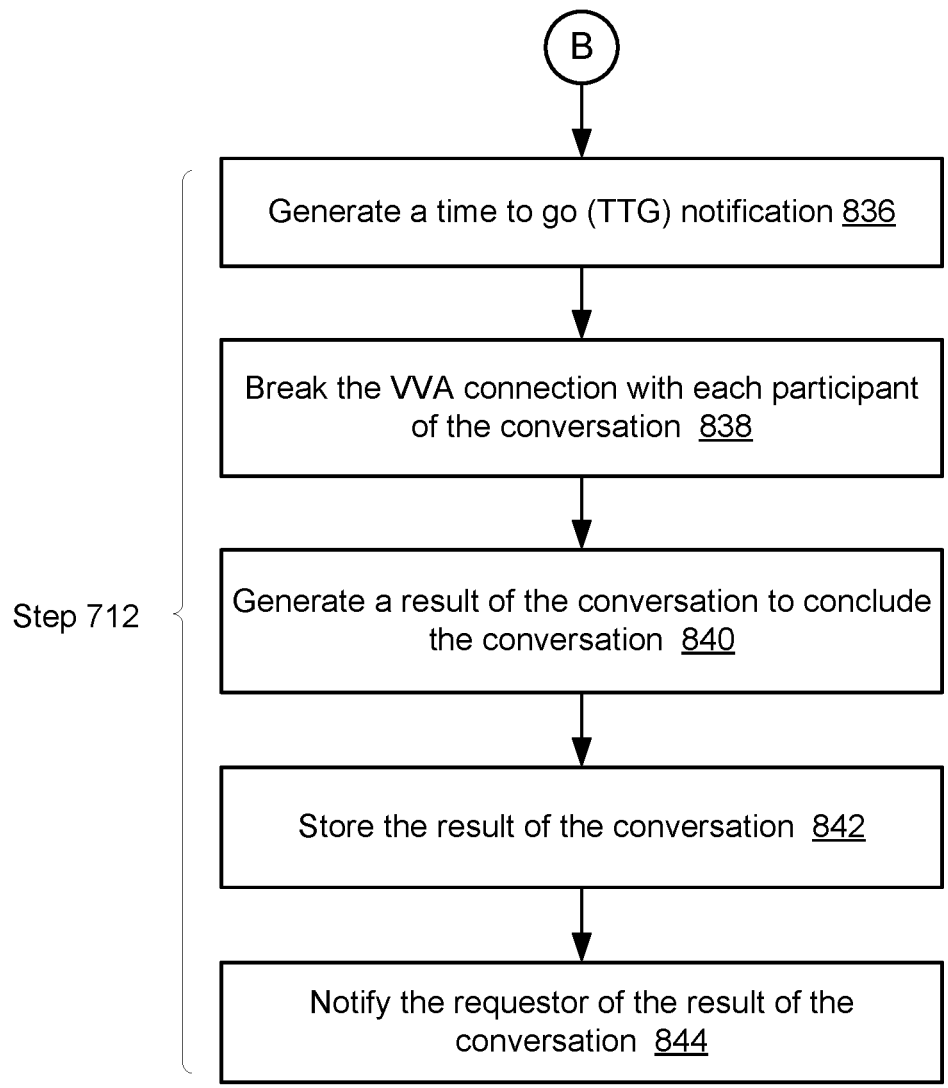

FIGS. 8A-8C illustrate a flowchart of another example method 800 for executing a proactive conversation. At step 802 of FIG. 8A, the scheduler 259 triggers a conversation scheduled for a senior/user upon detecting an event associated with the conversation. For example, the scheduler 259 detects a calendar event showing that a specific time previously scheduled for the conversation arrives, and triggers the conversation.

Steps 804-812 of FIG. 8A correspond to step 706 of FIG. 7, where the conversation initiator 263 initiates the proactive conversation. Responsive to the conversation previously configured or scheduled for the user being triggered by the scheduler 259, at step 804, the conversation initiator 263 retrieves/determines information associated with the conversation, for example, retrieves a corresponding conversation object (e.g., the example object shown in FIG. 6) to obtain the information (e.g., participant information) needed to initiate the conversation.

At step 808, the conversation initiator 263 communicates with a VVA associated with the senior/user to invite the senior/user to join the conversation, i.e., the senior/user is called to confirm that she/he would like to join this previously scheduled group conversation. At step 810, based on the obtained participant information and responsive to the senior/user's confirmation, the conversation initiator 263 communicates with one or more VVAs associated with one or more participates to invite the participants to join the conversation. Once the senior/user and the one or more participants have agreed to join the conversation, at step 810, the conversation initiator 263 establishes a VVA connection with each participant of the conversation.

At step 812, the conversation initiator 263 further communicates with a natural language understanding (NLU) module 223 to train conversation-based natural language understanding. The conversation-based natural language understanding (NLU) training, in some embodiments, includes two procedures: 1) classifying an entity into a category and associate the entity with a tag, and 2) assigning a word with a topic. For example, with the first procedure, Andy may be classified and tagged as a caregiver for the senior Mary Smith shown in the conversation object of FIGS. 5 and 6, and Vince may be classified and tagged as the deceased husband of Mary Smith. With the second procedure, Casablanca may be considered as a movie topic. The NLU module 223 as well as the NLU training will be described in detail below with reference to FIGS. 9 and 10A-10C. Once the conversation initiator 263 transmits the NLU training result generated by the NLU module 223 to the conversation conducting module 265, the conversation initiation process ends.

Steps 814 and 816 of FIG. 8B correspond to step 708 of FIG. 7, where the conversation conducting module 265 enables the proactive conversation to be smoothly conducted. To do so, at step 814, the conservation conducting module 265 greets and instructs each participant of the conversation to converse on a topic. For example, the conversation conducting module 265 may receive tags associated with each participant and greet them differently based on the associated tags. The conversation conducting module 265 may also ask each participant to talk about the proposed topic, e.g., the soap opera Young and Restless as shown in FIG. 6). At step 816, the conversation conducting module 265 maintains the VVA connection with each participant of the conversation throughout the conversation such that the group conversation among the participants can proceed smoothly.

Steps 818-834 of FIG. 8B correspond to step 710 of FIG. 7, where the IMP 225 monitors and facilitates the proactive conversation in parallel with the conversation conducting step performed by the conversation conducting module 265 described above. The steps 818-834 outline the functionality that the IMP 225 may implement for monitoring and facilitating a conversation. More details about the IMP 225 will be described below with reference to FIGS. 11-15.

At step 818 of FIG. 8B, the IMP 225 receives a dialog act of the conversation. The dialog act contains audio, video or text of the conversation that has been recognized. At step 820, the IMP 225 communicates with the NLU module 223 to apply NLU processing on the dialog act, for example, identifying a topic that has been discussed by a participant in the last few minutes in the conversation. At step 822, the IMP 225 applies sentiment analysis on the dialog act, for example, identifying negative sentiment of some participants. At step 824, the IMP 225 detects a question from the dialog act and responds to the question, for example, answering a question of "where is store AAA?" At step 826, the IMP 225 computes a conversation metric such as a participation rate, a pause length, etc. At step 828, the IMP 225 determines whether a correction action is needed based on the conversation metric. If the correction action is needed, the IMP 225 takes the correction action at step 830 and updates the conversation metric at step 832. For example, if the participation rate for some participants is below a threshold value, the IMP 225 may change the subject under discussion in the conversation. If the correction action is not needed, the IMP 225 determines whether there is another dialog act at step 834. If yes, the method goes back to step 818 where the IMP receives a new dialog act. Otherwise, the method goes to step 836 where the conversation evaluator 227 starts to work.

Steps 836-844 of FIG. 8C correspond to step 712 of FIG. 7, where the conversation evaluator 227 concludes the proactive conversation. At step 836, the conversation evaluator 227 detects an end of the conversation and generates a time to go (TTG) notification. Responsive to the TTG notification, at step 838, the conversation evaluator 227 communicates with the conversation conducting module 265 to break the VVA connection with each participant of the conversation. At step 840, the conversation evaluator 227 generates a result of the conversation (e.g., a report) to conclude the conversation. In some embodiments, the conversation evaluator 227 also stores the result of the conversation at step 842 and notifies the requestor of the result of the conversation at step 844. Steps 836-844 will also be described in detail with reference to FIG. 16.

The NLU module 223 includes hardware, software, and/or firmware that process and analyze natural language data. As illustrated in FIG. 2C, the NLU module 223 may include a named entity recognition (NER) module 267 and a topic classifier (TC) module 269. In some embodiments, the NER module 267 may perform NER training to classify an entity into a category, and the TC module 269 may perform TC training to assign a word to a topic. FIGS. 9 and 10A-10C describe the functionality implemented by the NER module 267 and the TC module 269.

Figure 9:
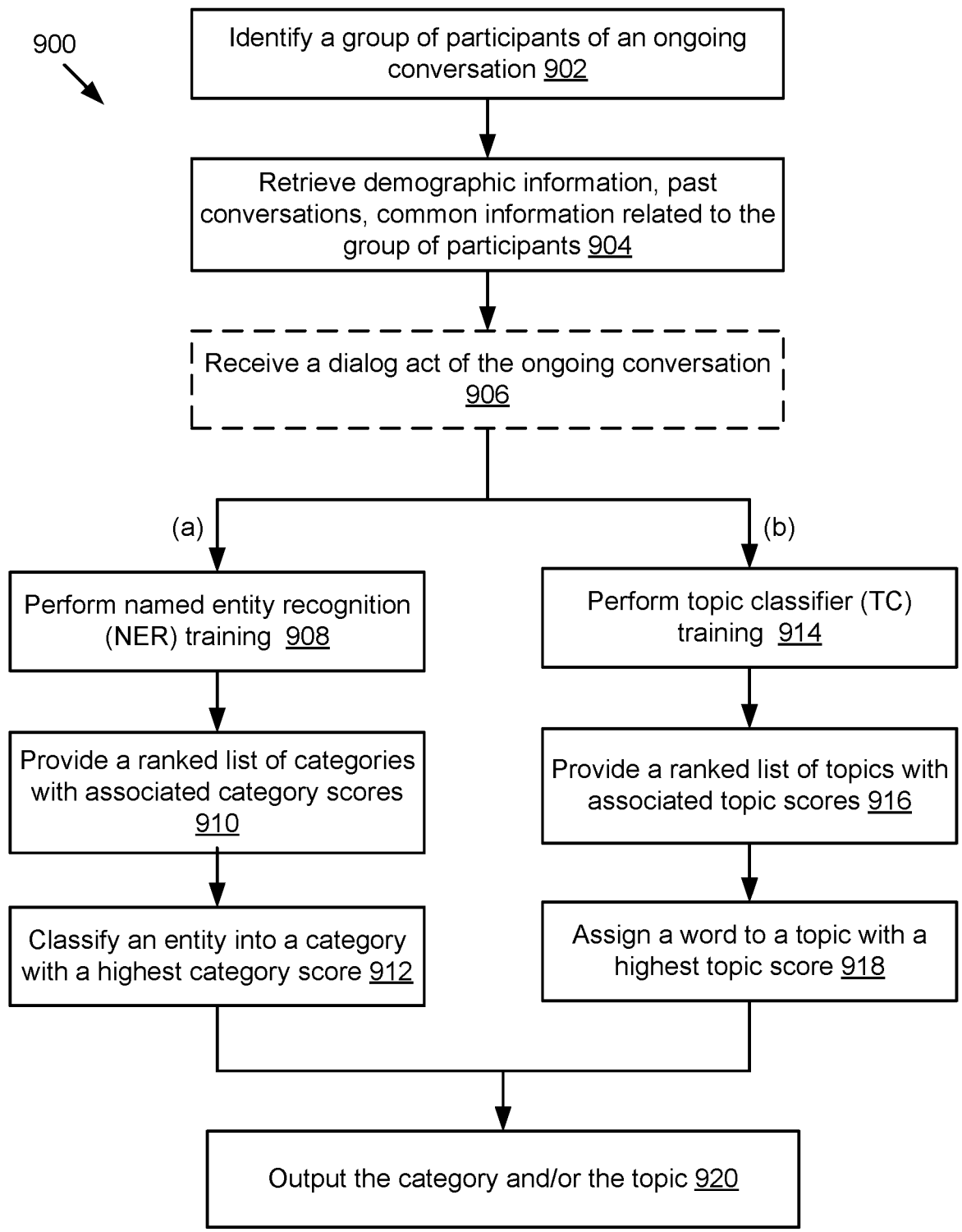
FIG. 9 is a flowchart of an example method for performing a conversation-based natural language understanding training.

FIG. 9 is a flowchart of an example method 900 for performing a conversation-based natural language understanding training. In some embodiments, the NLU module 223 may communicate with other components of the conversation facilitation server 103 (e.g., the conversation manager 221) to identify a group of participants of an ongoing conversation at step 902, and to retrieve demographic information, past conversations, common information related to the group of participants (e.g., participant characteristic) from the database 208 at step 904. Step 906 depicted with a dashed line is optional because the NLU module 223 may or may not receive a dialog act of the current conversation depending on whether the conversation is in an initiation stage as indicated by step 706. The dialog act is a data element that contains audio, video, or text data that has already been recognized by the VVED module 211. If the NLU module 223 receives a dialog act, the NLU module also performs NLU training on the dialog act.

As illustrated in FIG. 9, the NLU training includes (a) NER training procedure and (b) TC training procedure, which are implemented in parallel. The NER module 267 performs procedure (a) by performing NER training at step 908, providing a ranked list of categories with associated category scores at step 910, and classifying an entity into a category with a highest category score at step 912. The classification includes tagging the entity with a specific tag. The TC module 269 performs procedure (b) by performing TC training at step 914, providing a ranked list of topics with associated topic scores at step 916, and assigning a word to a topic with a highest topic score at step 918. At step 920, the NLU module 223 outputs the training result, i.e., the category associated with an entity and/or the topic assigned to a word.

In some embodiments, the NER module 267 may perform NER training procedure (a) using a long short term memory (LSTM) model to assign an entity with a tag. The NER is an information extraction task that seeks to locate and classify a named entity included in unstructured text, e.g., data from a conversation, into pre-defined categories. An entity may be a location (LOC), a person (PER), an organization (ORG), and other entities (MISC). However, not every word of the text, e.g., the word "so," "see," "here," can be assigned with an entity tag, and, in this case, the NER module 267 may associate this word with a no-entity tag "O." Additionally, since some entities such as "San Francisco" contain multiple words, the NER module 267 may tag the beginning word as "B-" and subsequent "inside" words as "I-."

In some embodiments, the NER module 267 may use a dictionary when classifying an entity into a category or assigning the entity with a tag. However, because a dictionary includes only a finite number of words, the NER module 267 may tag a word that does not occur in a dictionary as a known entity based on the context, e.g., other words that surround the specific word, which can be complicated and challenging. As a result, the NER module 267 may use a LSTM model as a general purpose solution for assigning entity tags, and supplement the LSTM model with specialized dictionaries derived from the demographic information for each participant in a conversation such that both a general word as well as a specific word from a conversation can be assigned with an entity tag. In some embodiments, the NER module 267 may build the LSTM model in four steps.

The first step is to determine word representation. For each word, the NER module 267 may build a vector $\underline{w}$ in $R^n$. This vector is a concatenation of word embeddings and character level features extracted with a bi-directional LSTM at the character level. The word embeddings are from a learning algorithm, for example, Stanford GloVe Project.

The second step is to determine contextual word representation: Given the word representations $\underline{w}$, the NER module 267 may run a bi-directional LSTM over the sequence of word vectors to obtain another sequence of vectors $\underline{h}$ in $R^k$.

The third step is decoding. Responsive to associating each word $\underline{w}$ with a vector $\underline{h}$ that captures information from the word, including its characters and its context, the NER module 267 may input the word $\underline{w}$ and the associated vector h to a fully connected neural network. The neural network computes a score for each tag assigned to each word.

The fourth step is dictionary lookup. The NER module 267 may replace each word tagged as PER with a corresponding relationship tag for a given dialog act initiated by a particular participant in the conversation. This provides subsequent steps of the text generation algorithm with a combination of general purpose information about named entities and specific information about people who are being discussed.

In some embodiments, the NER module 267 may train the LSTM model to produce a "NER network" with a cross entropy loss function in a deep learning system (e.g., Tensorflow deep learning system). In some embodiments, the NER module 267 may perform a final prediction with Viterbi decoding in python. In some embodiments, the NER module 267 may perform the dictionary lookup step after decoding is finished.

Figure 10A:
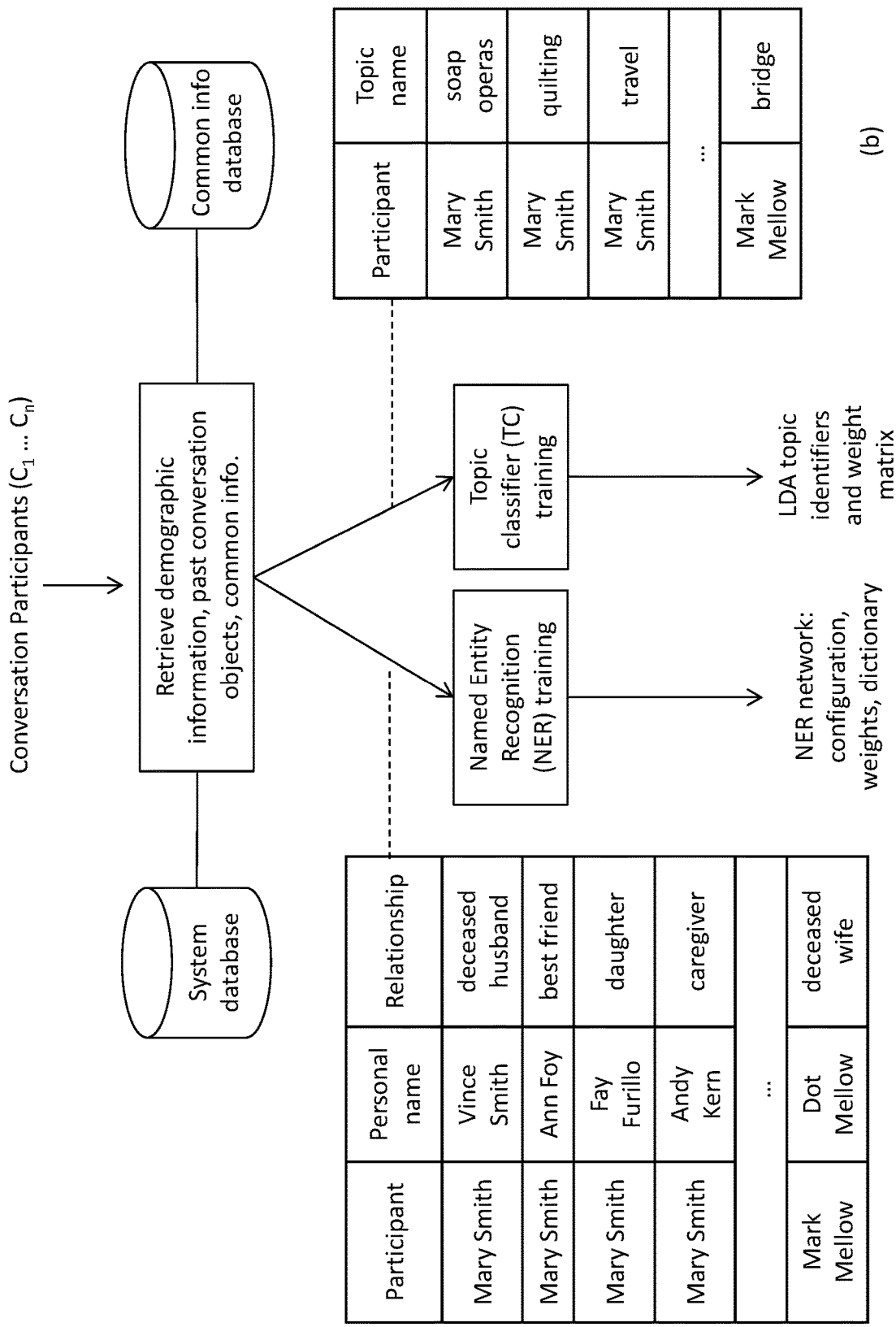
FIG. 10A is a diagram illustrating a procedure of a conversation-based natural language understanding training.

In some embodiments, when training the LSTM model, the NER module 267 may bias a personal relationship known to a conversation participant so that this relationship receives a higher weight than similar categories that could also apply. FIG. 10A (a) shows the NER training procedure and result, where the NER module 267 ranks Vince Smith higher as a deceased husband than as a person because he is listed as a deceased husband in Mary Smith's demographic information.

After training the NER network, comprised of a stacked bi-directional recurrent neural network with long short-term memory units that transform word features into named entity category/tag scores, the NER module 267 may store its configuration (e.g., levels, nodes per level) and weights in the database 208. At run time, the NER module 267 may classify each word in the text of a conversation (e.g. a dialog act) by the long short term memory-convolutional neural network (LSTM-CNN) by its output layers. In FIG. 10C (a), an example process of applying the NER training to the phrase "I saw Casablanca at Loews Tech with Vince in 1948" is shown. The NER module 267 receives the phrase as input text and passes it through the NER network, where the tag of each word is written. For example, "Vince" 1008 may be classified as a person and tagged as "B-PER." The tags are then re-written by the dictionary lookup step, thus incorporating both general purpose information from the NER network and specialized information from demographic information and past conversations. For example, "Vince" 1010 is now modified to be a deceased husband and tagged as "B-Deceased Husband."

It should be noted that specialized information, such as the first mention of a deceased spouse, can be remarkably effective cues for generating a conversational prompt. When this occurs, interjecting "Mary, would you like to tell us more about Vince?" can trigger a flood of memories and conversation topics that would not have occurred otherwise. The fact that Mary herself has mentioned Vince indicates that she is likely comfortable with discussing their relationship. Classifying an entity into a category and assigning the entity with a tag in the NER training, e.g., classifying Vince as deceased husband and tagging Vince with "B-Deceased Husband," is therefore advantageous because there may not exist a way to detect that Mary has mentioned her husband other than applying the hybrid global/local approach for NER described above.

Figure 10B:
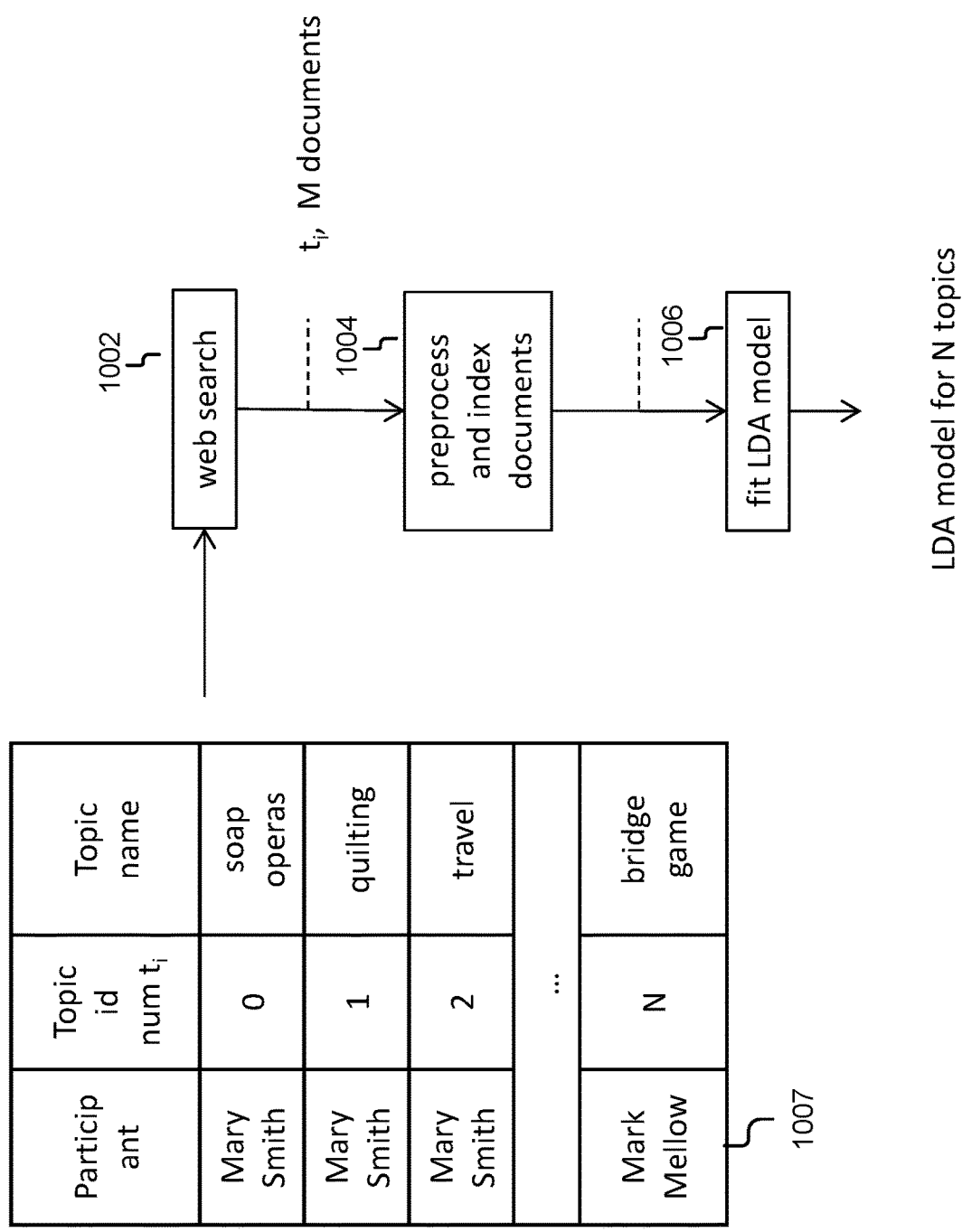
FIG. 10B is a diagram illustrating a procedure of Latent Dirichlet Allocation (LDA) topic classifier training.
Figure 10C:
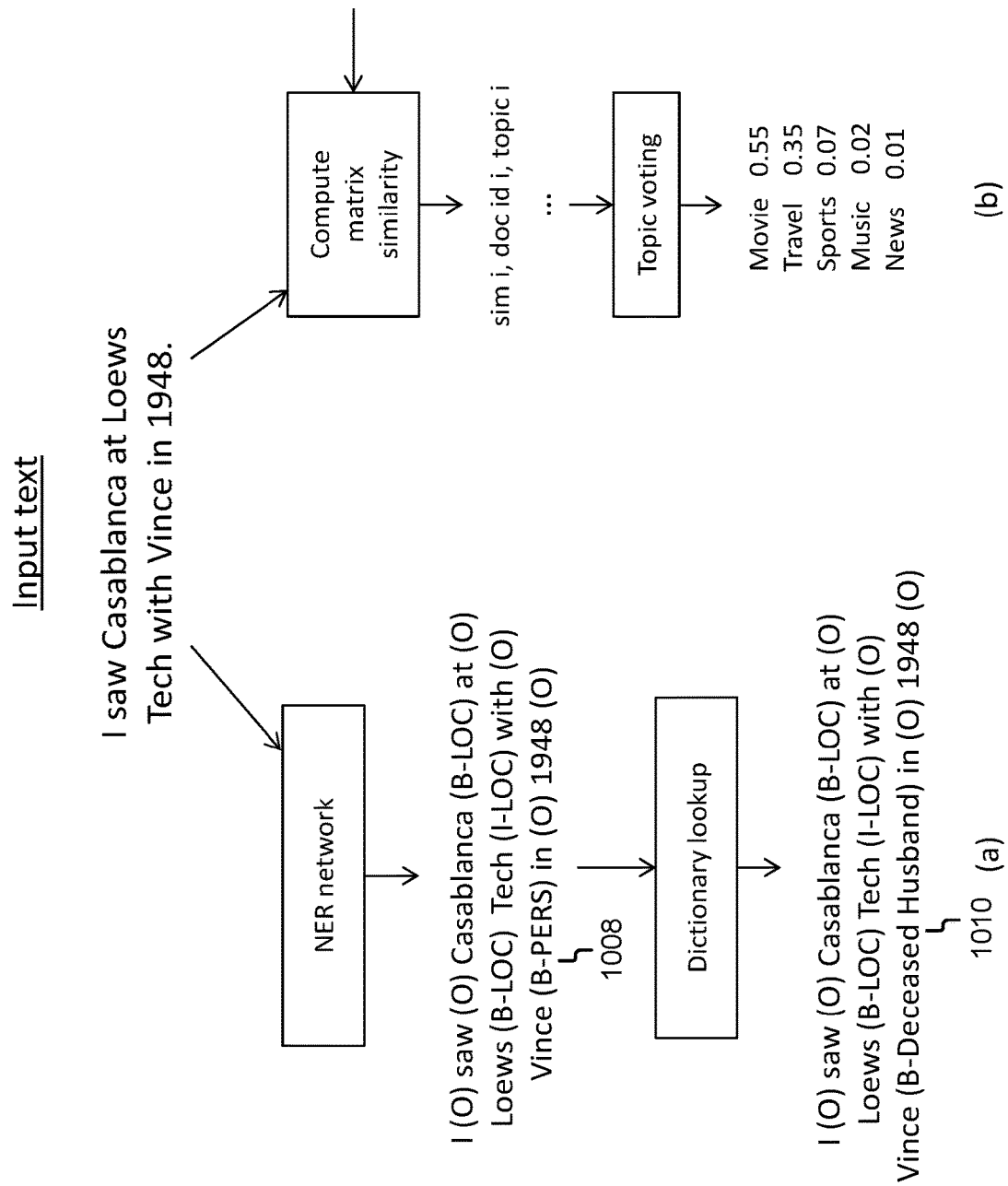
FIG. 10C is an example result of a conversation-based natural language understanding training.

When the NER module 267 performs NER training for a conversation, the TC module 269 also performs TC training in parallel as shown in FIGS. 10A-10C. As illustrated in FIG. 10A (b), the TC module 269 trains a specialized topic classifier. In some embodiments, the TC module 269 may use a Latent Dirichlet Allocation (LDA) technique to perform the TC training. LDA has its foundation in probabilistic graphical models (PGM). LDA posits that each document is a mixture of a small number of topics and that the presence of each word is attributable to topics of one of the document. In some embodiments, LDA is based on a matrix factorization technique. Based on the LDA technique, the TC module 269 represents a collection of documents as a document-term matrix in vector space, and converts the document-term matrix into two lower dimensional matrices—M1 and M2. M1 is a document-topics matrix and M2 is a topic-terms matrix with dimensions (N, K) and (K, M) respectively, where N is the number of documents, K is the number of topics, and M is the vocabulary size. The TC module 269 further iterates through each word "w" for each document "d" and tries to adjust the current topic-word assignment with a new assignment. The TC module 269 may assign a new topic "k" to word "w" with a probability P.

In some embodiments, the TC module 269 may compute the probability P as a product of two probabilities p1 and p2 determined for each topic. The TC module 269 may compute p1=p (topic t|document d), which is the proportion of words in document d that are currently assigned to topic t, and compute p2=p (word w|topic t), which is the proportion of assignments to topic t over all documents that come from this word w. Next the TC module 269 may update the current topic-word assignment with a new topic with the probability P, the product of p1 and p2. When performing this step, the TC module 269 may assume that all the existing word-topic assignments except the current word are correct. This is essentially the probability that topic t generated word w. After a number of iterations, the TC module 269 may determine that a steady state is achieved where the document topic and topic term distributions are fairly good, which is considered as the convergence point of LDA.

In some embodiments, the TC module 269 may use a gensim package in python to estimate the LDA matrices for texts associated with the topics known to be favorites of each conversation participant, as shown in FIG. 10A (b). The TC module 269 may also use general purpose texts associated with topics that are commonly known such as movies, sports, music, news, fashion, shopping, etc. When the TC module 269 trains the LDA matrices, the TC module 269 may specify the total number of possible topics as the sum of the number topics known to each conversation participant as shown in FIG. 10A (b) and the number of general purpose topics. The TC module 269 may label the keyword vectors returned by the LDA training procedure with the topic names they correspond to, including in the illustrated example soap operas, quilting, travel, bridge, movies, sports, music, news, fashion, shopping, etc.

FIG. 10B is a diagram illustrating a procedure of LDA topic classifier training. The LDA technique may exceed in processing long documents, however, the TC module 269, in the current application, monitors and processes casual conversations, i.e., short dialog acts with limited text that often concern topics known to a group of senior citizens based on their past life experiences (e.g., hobbies, interests, children, travels, etc.). As a result, the TC module 269 adds a web search step at 1002 before actually performing LDA modeling at steps 1004 and 1006 as shown in FIG. 10B. The database 208 stores the life experience data of each senior/user received from a survey/interview for the senior/user when they first enroll (e.g., at a conversation setup stage) or when they are added to the conversation facilitation system 101. The seniors can also indicate the conversation topics they are interested in on a web form. The TC module 269 uses each topic as a "seed" for a web search that retrieves M documents. In some embodiments, the TC module 269 may communicate with the VVA 101 and other components of the system 100 (e.g., the VVA 101) to interactively perform the web search with the senior or with the assistance of a caregiver so that each topic can be associated with a set of M documents that truly reflect the conversation topic. The web search 1002 is advantageous because it helps improve relevancy, accuracy as well as efficiency of topic classification. For example, as shown in FIG. 10B, given Mark Mellow being interested in bridge 1007 and without the web search at step 1002, the TC module 269 may retrieve many documents about civil engineering structures instead of getting the result related to Mark's real interest in "bridge game."

Once M documents are retrieved for each topic at step 1002, the TC module 269 may preprocess each document by splitting it up into tokens (one per word) that are all in lower case. The TC module 269 may then construct an index that assigns a unique id to each preprocessed document. The TC module 269 may also retain a mapping between document ids and topic id numbers. In some embodiments, the TC module 269 may fit an LDA model to the data for the given number of topics (M).

Referring now to FIG. 10C (b), at run time, the TC module 269 may apply topic classification to each dialog act with a matrix similarity between the input text and the LDA model, and output a list of document ids sorted in a decreasing order of their similarity to the input text as well as the original topic id for the web search query that is used to retrieve that document. The results including the list of documents and the original topic id may then be used in a topic voting procedure, where the TC module 269 aggregates the results and outputs a ranked list of labeled topic names associated with the dialog act. For example, the phrase "I saw Casablanca at the Loews Tech in 1948" is assigned to the Movie topic with a likelihood 0.55, the Travel topic with a likelihood 0.35, and all other categories with a likelihood less than 0.10. As a result, the TC module 269 determines that this phrase/dialog act is either about a movie or about travel.

FIG. 2C illustrates that the SC 203 also includes an interactive management platform (IMP) 225 that monitors and facilitates a conversation. As illustrated in the figure, the IMP 225 may include a dialog manager 271, and the dialog manager 271 may further include a sentiment analyzer 273, a question responder 275, a performance management module 277, a topic tracker 279, a mood tracker 281, a conversation prompt generator 282, and an action engine 283. The conversation prompt generator 282 is depicted in dashed-lines to show that it may be a component separate from the action engine 283 or may be part of the action engine 283.

Figure 11:
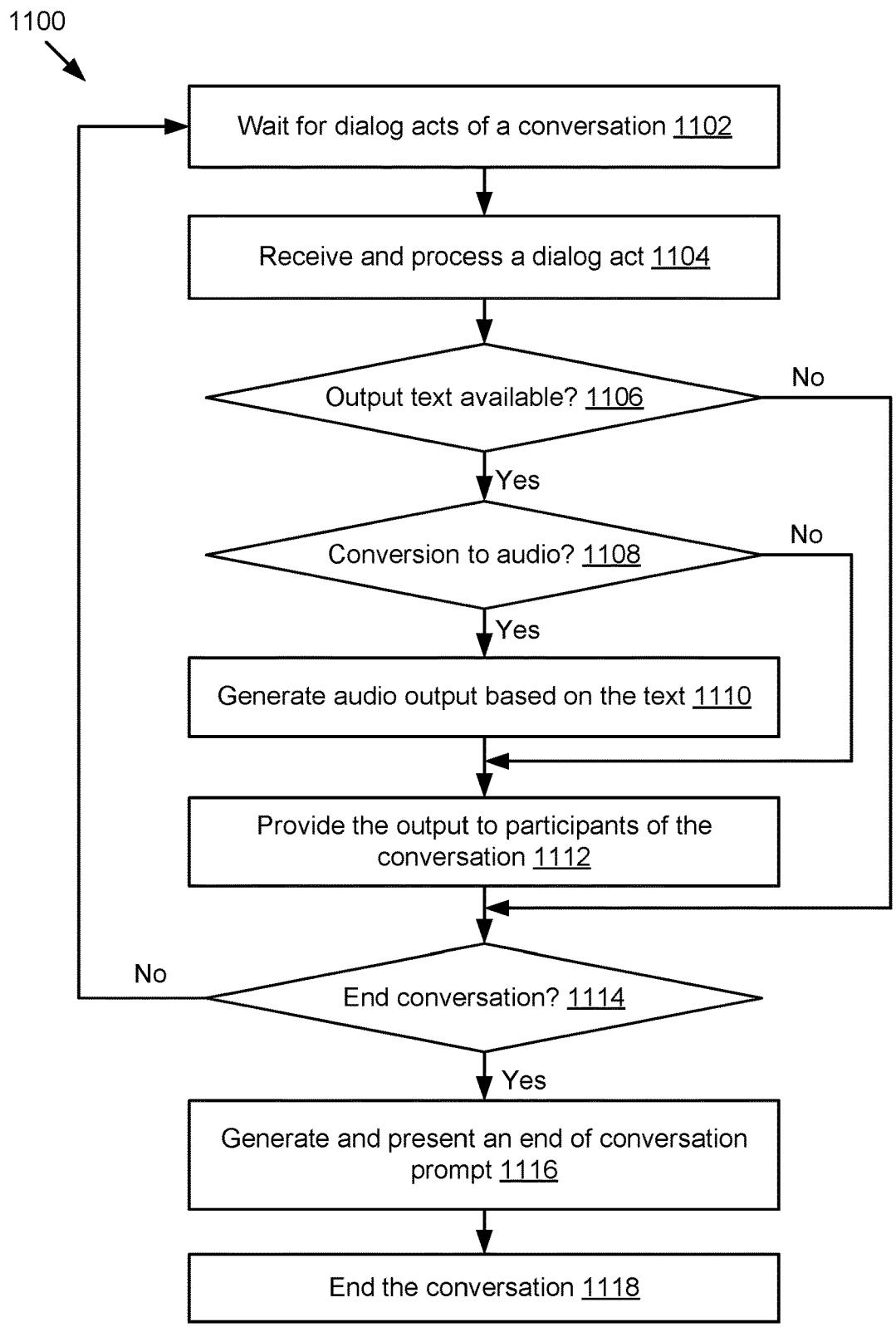
FIG. 11 is a flowchart of an example method for managing and processing a dialog act.

FIG. 11 is a flowchart of an example method 1100 for managing and processing a dialog act. At step 1102, the dialog manager 271 waits for dialog acts of a conversation. Usually when a conversation is initiated, the conservation conducting module 265 maintains an open VVA connection with each participant of the conversation for participant(s) to converse on a proposed topic. The dialog manager 271 may receive a dialog act based on participant(s) conversing. A dialog act is a time-stamped data element that contains raw audio or video data or text from audio that has already been recognized. The raw audio or video data is recognized by the VVED module 211. For example, the VVED module 211 may use voice recognition application(s) such as that provided by Amazon® or Google® to transcribe the raw audio or video data to text. The dialog act may also identify the conversation object it is associated with, a participant who spoke the text, and an identifier identifying the device that captured the data.

At step 1104, the dialog manager 271 receives and processes a dialog act. At step 1106, the dialog manager 271 determines whether output text is available, for example, whether there is an answer for a question asked by a participant in the dialog act. If there is no output text, the method moves to step 1114. If there is output text, the dialog manager 271 determines, at step 1108, whether a conversion to audio is needed. If there is no need to convert the text to audio, the dialog manager 271 provides the output to participants of the conversation at step 1112. Otherwise the dialog manager 271 communicates with other components of the system 100 to generate audio output based on the text at step 1110 and provides the output to participants of the conversation at step 1112.

At step 1114, the dialog manager 271 determines whether to end the conversation. If no, the method moves back to step 1102 to wait for the next dialog act. If yes, the dialog manager 271 generates and presents an end of conversation prompt at step 1116 and ends the conversation at step 1118. In some embodiments, the dialog manager 271 may incorporate with the conversation conducting module 265 and the conversation evaluator 227 to end the conversation.

Figure 12:
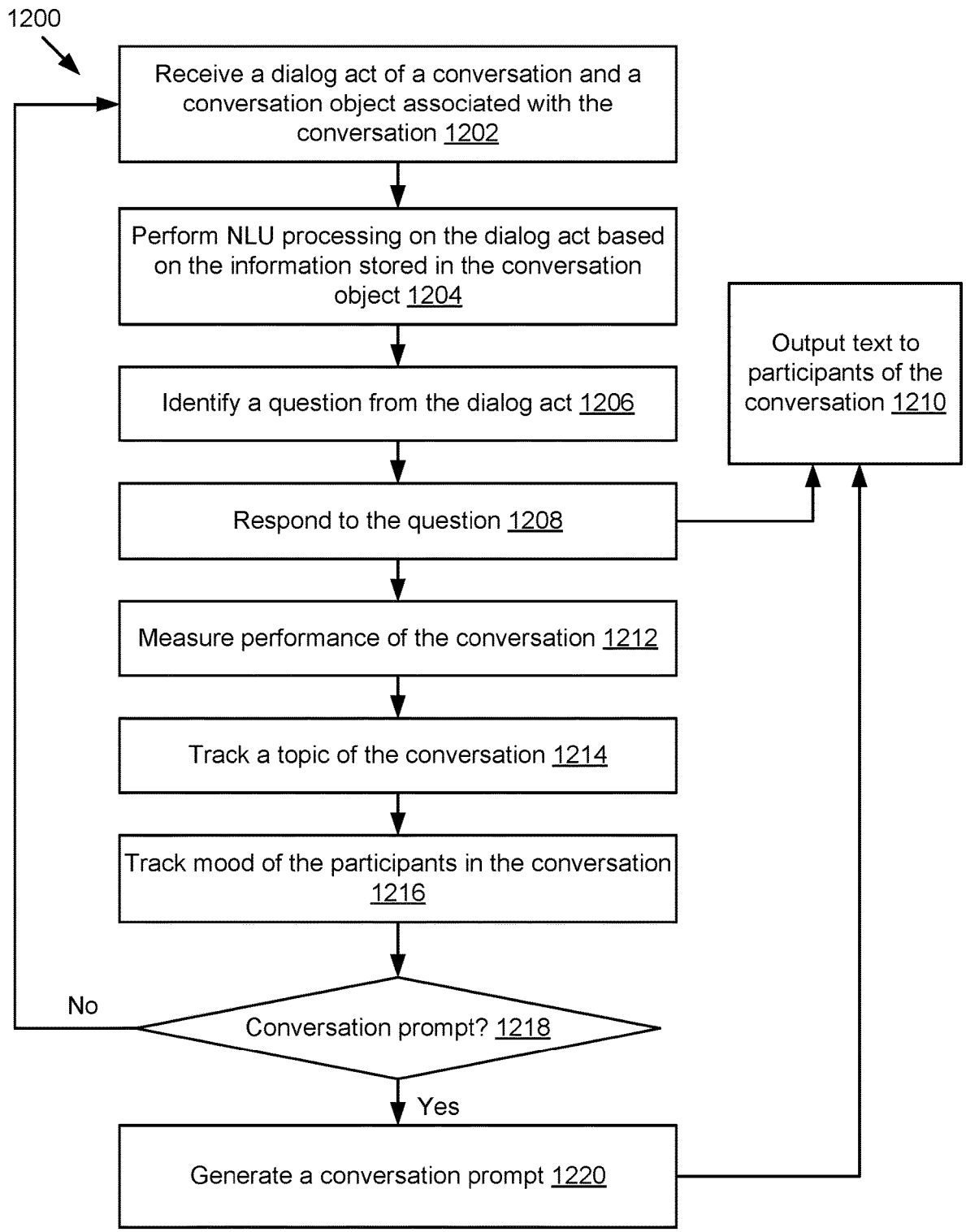
FIG. 12 is a flowchart of an example method for monitoring and facilitating a conversation.

FIG. 12 is a flowchart of an example method 1200 for monitoring and facilitating a conversation, which is performed by various components of the dialog manager 271 included in the IMP 225 in communication with other components of the conversation facilitation system 100.

At step 1202, the dialog manager 271 receives a dialog act of a conversation and a conversation object associated with the conversation from the IMP 225. At step 1204, the dialog manager 271 communicates with the NLU module 223 to perform NLU processing on the dialog act based on the information stored in the conversation object. For example, the dialog manager 271 incorporates with the NLU module 223 to apply natural language understanding (NLU) processing to the text in the dialog act. This NLU processing, as described above, may include topic classification using a specialized LDA tuned for topics favored by the participants in the conversation, and a specialized named entity recognition using CNN-LSTMs specialized for the named entities favored by the participants in the conversation.

In some embodiments, the NLU processing may also include sentiment analysis, which is implemented by the sentiment analyzer 273 included in the dialog manager 271 in communication with the NLU module 223. The sentiment analyzer 273 may communicate with the NLU module 223 to compute a sentiment analysis score for each dialog act using the Stanford Core NLP Processing toolkit and the python Natural Language Toolkit. Based on this sentiment analysis algorithm, the sentiment analyzer 273 may assign a positive score to a dialog act if its sentiment is considered positive and assign a negative score to a dialog act if its sentiment is considered negative, and use the value of the score to reflect the sentiment strength. For example, the sentiment analyzer 273 may determine a sentiment analysis score of 1.32 for a dialog act of "My daughter Ann is so smart. She just graduated from Stanford. I'm super proud of her," while determining a sentiment analysis score of −1.55 for the phrase "My son Bob is a bum. He was arrested again for dope possession and burglary."

The dialog manager 271 includes a question responder 275. At step 1206, the question responder 275 identifies a question from the dialog act, and at step 1208, responds to the question. In some embodiments, the question responder 275 may apply pattern matching on the text of the dialog act and detect a trigger key phrase such as "Care system . . . " or "Amy . . . " where Care system is the name of the conversation facilitation system 100 and Amy is one of many possible personal names associated with the system 100. Responsive to detecting a question, the question responder 275 forwards the question to a service to obtain an answer. The service may be EVI service provided by Amazon®, which answers factual questions like "what time is sunset today?" If no answer is found, the service returns either "I don't have an opinion on that" or "I don't know about that." The question responder 275 receives the answer/text from the service and adds the text to the conversation object associated with the conversation. At step 1210, the question responder 275 also communicates with other components of the system 100 to place the text in a queue and output the text to participants of the conversation. In some embodiments, the question responder 275 in communication with other components of the system 100 may remove the text/conversation objects from the queue, apply the text to speech conversion (e.g., using a conversion software) to the text, and route the voice output to the conversation participants.

The dialog manager 271 also includes a performance management module 277. At step 1212, the performance management module 277 measures performance of the conversation. In some embodiments, the performance management module 277 may calculate and update conversation metric(s) for an ongoing conversation. The conversation metric(s) include a participation rate and a pause length. The participation rate measures the percentage of dialog acts in the previous N minutes attributable to each participant over a moving window of the previous M (M>N) minutes. For example, N=5 and M=10, where five minutes of conversational interchange may be sufficient to begin accumulating reliable statistics with a reasonable ten minute window. FIGS. 13A and 13B show the participation rate for a four person conversation. As shown in FIG. 13A, the average expected participation rate for each person is between the lower limit 15% and the upper limit 35%. If the participation rate for any individual is outside these bounds, the performance management module 277 determines that the conversation is unbalanced, and communicates with an action engine 283 to take a correction action to rebalance the conversation exchange between participants. The action engine 283, also contained in the dialog manager 271, includes hardware, software, and/or firmware that performs a correction action in response to receiving a signal from other components of the SC 203. FIG. 13A shows a balanced conversation which does not require a correction action, while FIG. 13B shows a conversation that is unbalanced, where Greg is clearly dominating the conversation, Jan is barely within limits, and Marcia and Cindy are well under the lower limit of acceptable participation.

The performance management module 277 may also monitor the time between dialog acts in a conversation, and determine a pause length by computing a difference between timestamps of consecutive dialog acts as stored in the conversation object. In some embodiments, the performance management module 277 may accumulate the history of time gaps between dialog acts as expressed in a moving window over the previous N minutes (e.g., ten minutes) and determine pause length(s) at different stages of the conversation. FIG. 13C shows a plot of pause lengths, e.g., time gaps between dialog acts. The performance management module 277 may further use two parameters, a correction threshold and a correction gap, to evaluate the performance of the conversation in terms of the pause length. For example, in FIG. 13C, the performance management module 277 sets the correction threshold to be 15 seconds and sets the correction gap to be five dialog acts. If a time interval between dialog acts, i.e., a pause length, is greater than the correction threshold seconds (15 seconds) for more than the correction gap dialog acts (5 dialog acts), the performance management module 277 may determine that the conversation is slowing down and consequently communicate with the action engine 283 to take a correction action. As shown in FIG. 13C, the performance management module 277 determines that a conversation has slowed down because more than five dialog acts have occurred that are more than 15 seconds apart.

The dialog manager 271 also includes a topic tracker 279. At step 1214, the topic tracker 279 tracks topics of the conversation, and records and maintains a stack of topics that have been discussed. The records of the topics also include the time stamps of each dialog act in which each topic was discussed, the originator of each dialog act (the person who spoke it), and an amount of time each topic was discussed, etc. FIG. 14A shows an example stack of topics recently discussed in a conversation, which demonstrates that Greg has been talking about his daughter Ann for the last 31 minutes or more, and that, before Greg's talking, Jan originated a discussion about bridge that lasted for only three minutes.

The dialog manager 271 also includes a mood tracker 281. At step 1216, the mood tracker 281 tracks mood of the participants in the conversation. In some embodiments, the mood tracker 281 may communicate with the sentiment analyzer 273 to track and record the sentiment analysis result at different stages of a conversation, for example, maintaining a rolling plot of the sentiment analysis of the dialog acts in the previous 30 minutes of the conversation. FIG. 14B shows an example of a conversation that started out positive and over time descended into having a negative sentiment. If the rolling sentiment analysis score computed by the sentiment analyzer 273 falls below the lower limit for longer than certain mood gap minutes, which is measured by the difference in timestamps on dialog acts, the mood tracker 281 may flag this conversation as requiring a correction action. In this case, the mood tracker 281 may communicate with other components of the system 100 (e.g., the third party server 107, the action engine 283) to provide a joke and/or change to a new topic to turn this around.

The dialog manager 271 also includes a conversation prompt generator 282. At step 1218, the conversation prompt generator 282 determines whether a conversation prompt is needed. If needed, at step 1220, the conversation prompt generator 282 generates the conversation prompt, and communicates with other components of the system 100 to output text/the conversation prompt to participants of the conversation. Otherwise, the method 1200 goes back to step 1202 to receive a next dialog act of the conversation.

Based on the data received from the performance management module 277, the topic tracker 279, and the mood tracker 281, the conversation prompt generator 282 may apply a set of rules to determine whether to generate a prompt and to generate the prompt if needed. For example, the conversation prompt generator 282 may apply a set of rules to the participation rate and time between dialog acts (e.g., pause length) provided by the performance management module 277 and the result from the mood tracker 281 to determine whether to generate a prompt. If the conversation prompt generator 282 receives signals indicating that the single person participation rate is above an upper limit or the pause length is above an interjection threshold for longer than interjection gap minutes, or the sentiment analysis score is below a lower limit for longer than mood gap minutes, then the conversation prompt generator 282 generates a conversation prompt based on the received signals and the conversation object associated with the conversation.

In some embodiments, the conversation prompt generator 282 may also examine the conversation object and determine whether to generate a generic conversation prompt, a subject specific prompt related to the current subject under discussion, a different subject preferred by the conversation participant(s), or a joke. The conversation prompt generator 282 may preferably generate a joke when the received signal(s) indicate that the sentiment analysis score is trending down and/or the mood gap has been exceeded, for example, as shown in FIG. 14B. The conversation prompt may include content such as stories, music, advertisement, etc., and may be of a variety types such as text, audio, and/or video.

Responsive to selecting the subject of the response, the conversation prompt generator 282 may communicate with the NLU module 223 to generate a natural language passage of text with a recurrent neural network (RNN), using a sequence to sequence model enhanced with a subnetwork for the additional features of participation rate, gap between dialog acts, mood track, and track topic. The generation of the natural language passage of text with a RNN is also based on a database of past conversations that supplies training data that is continuously update over time, and reliable seed data obtained from well-known collections such as the Ubuntu dialog corpus, the Reddit data set, etc. The conversation prompt generator 282 may also communicate with the NLU module 223 to retain the responses provided by the network and the effect they had on the performance measurements over time, and use the information to periodically retrain the neural network.

Figure 15:
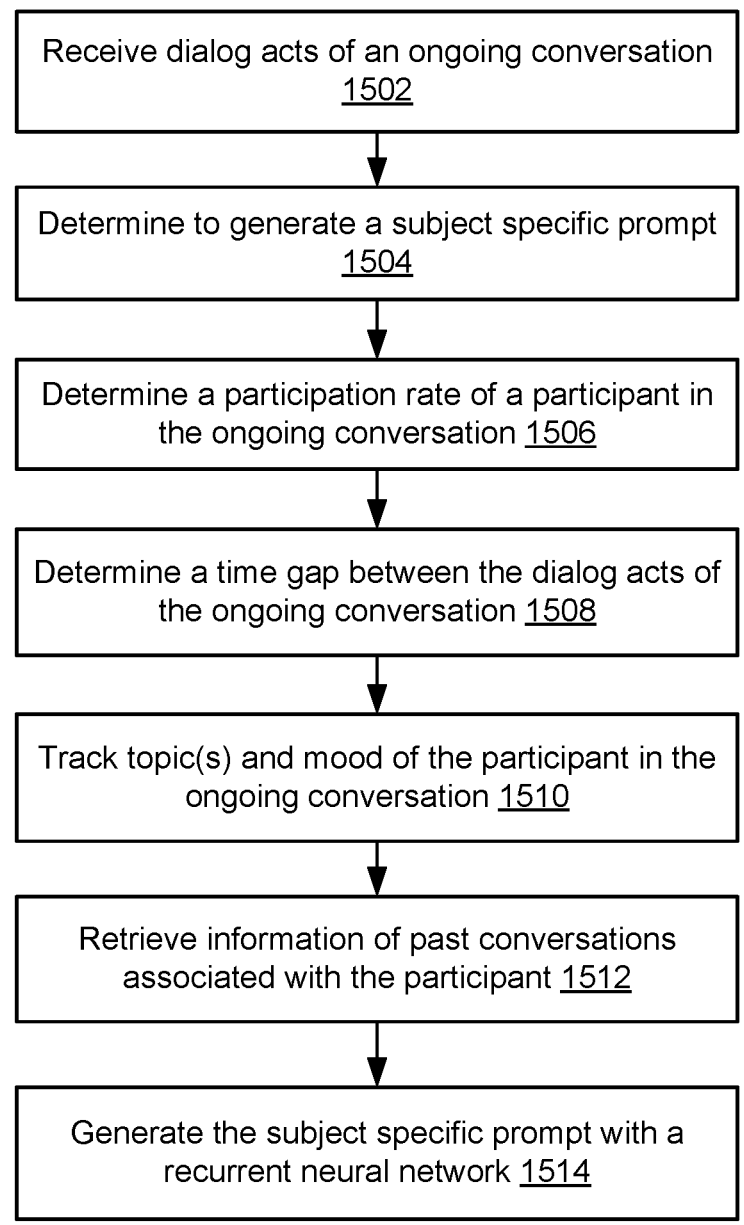
FIG. 15 is a flowchart of an example method for generating a conversation prompt.

FIG. 15 is a flowchart of an example method 1500 for generating a conversation prompt. At step 1502, the conversation prompt generator 282 receives dialog acts of an ongoing conversation. At step 1504, the conversation prompt generator 282 determines to generate a subject specific prompt. At step 1506, the performance management module 277 determines a participation rate of a participant in the ongoing conversation. At step 1508, the performance management module 277 determines a time gap between the dialog acts of the ongoing conversation. At step 1510, the topic tracker 279 and the mood tracker 281 track topics and mood of the participant in the ongoing conversation. At step 1512, the conversation prompt generator 282 retrieves information of past conversations associated with the participant. At step 1514, the conversation prompt generator 282 in communication with the NLU module 223 generates the subject specific prompt with a recurrent neural network.

Although the last step 1220 of FIG. 12 is to generate a conversation prompt (which is as also shown in FIG. 15), the steps for monitoring and facilitating a conversation are not necessarily performed in the sequence shown in FIG. 12. It should be understood some of these steps can be performed in parallel and/or the performing order can also be changed, i.e., it may take other forms and include additional or fewer components to achieve the functionality of monitoring and facilitating a conversation as shown in FIG. 12 without departing from the scope of the present disclosure.

In parallel with the IMP 225 monitoring and facilitating an ongoing conversation, a conversation evaluator 227 also works to determine whether to end and conclude the ongoing conversation. As illustrated in FIG. 2C, the conversation evaluator 227 may include a notification generator 285 and a result generator 287.

In some embodiments, the notification generator 285 may monitor the schedule of an ongoing conversation. The notification generator 285 may also monitor the temperament of the participant(s) of the conversation based on determining their voice stress and the amount they are participating in the conversation. When either the scheduled time for the conversation expires or the participant(s) becomes non-communicative or unhappy, the notification generator 285 generates a time to go (TTG) notification.

Once the TTG notification is generated, the notification generator 285 may transmit it to the IMP 225, and the IMP 225 may send a message or a conversation prompt to the participants that it is time to wrap up the conversation and they should say goodbye to one another. After a specified amount of time (e.g., 30 seconds), the notification generator 285 may also communicate with the conversation conducting module 265 to break the connections with the VVAs 101 associated with the participants to stop the conversation.

In some embodiments, after the conversation ends, the result generator 287 may generate a result of the conversation and store the result in the database 208. The result may include, but not limited to, an amount of time each participant spoke, a participation rate of a participant (e.g., computed based on the amount of time that a particular participant spoke divided by a total amount of time that all participants spoke), topics they discussed, the transcribed speech, voice stress, conversational temperament, jokes and associated responses, and other content that have been shown (e.g., music, ads).

Based on the conversation result, the result generator 287 may also send a message to the requestor of the conversation at the conclusion of each proactive conversation. The message includes at least the data specified in the "result format" field of the conversation object associated with the proactive conversation as shown in the example of FIG. 6.

Figure 16:
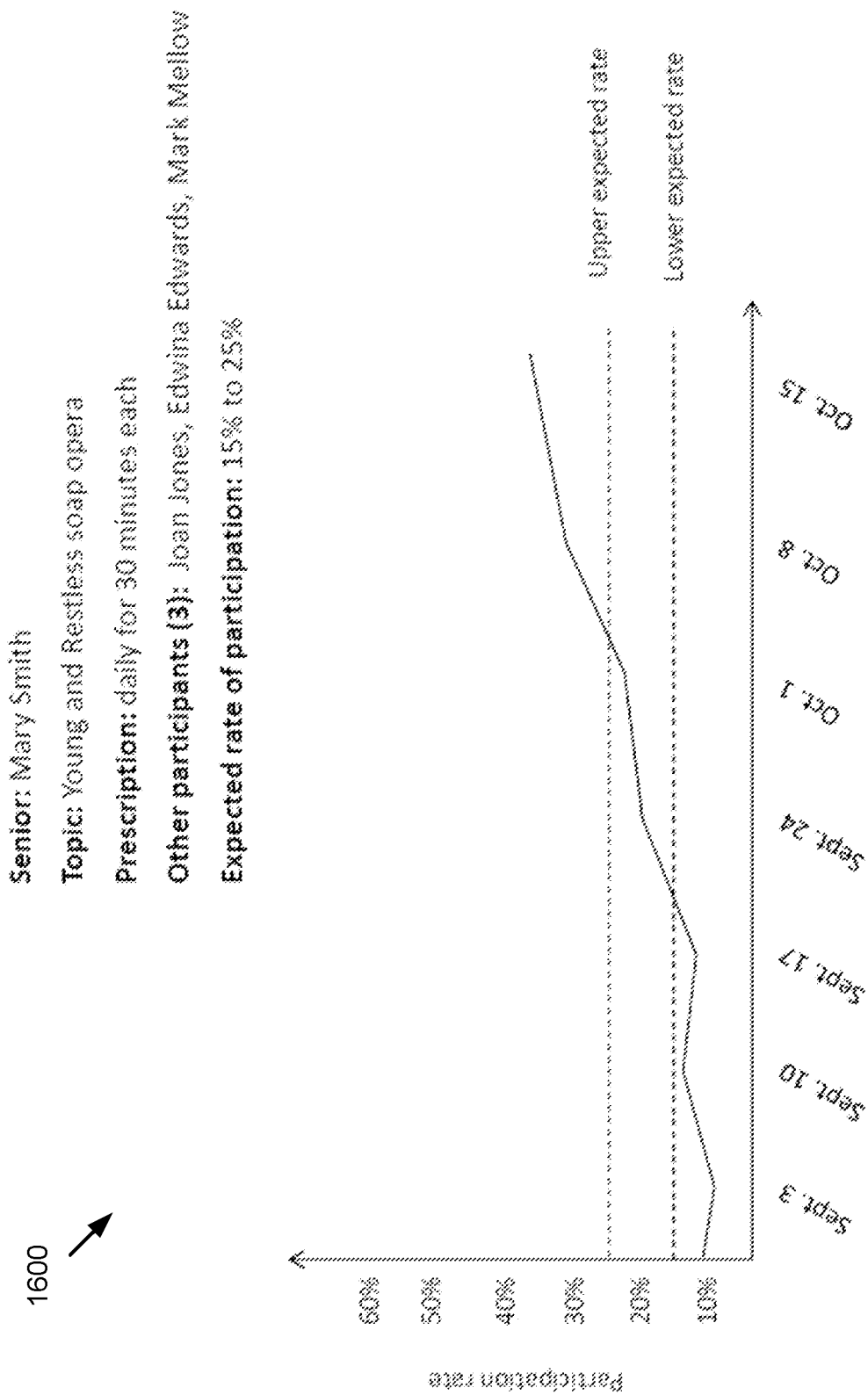
FIG. 16 is an example conversation result.

FIG. 16 shows an example conversation result 1600 generated from a recurring proactive conversation requested for the senior Mary Smith. The conversation result 1600 includes a graphical report that summarizes the participation rate of Mary Smith over time. Based on Mary's preferences (e.g., answers to questions as shown in the example conversation object of FIG. 5), the conversation is about the Young and Restless soap opera topic and three other participants joins the prescribed 30-minute conversation with her each day. The result generator 287 provides this report to the requestor for the conversation, Dr. Patty. The result generator 287 determines that an expected participation rate for a healthy senior should be between 15% and 25%. Although, between September 3 and September 17, Mary Smith did not participate enough, she improved and had results in the desirable range after about September 20. After about October 3 she started over performing and had a participation rate greater than 25%. The conversation result uses the participant's performance data during conversation(s) to provide explicit and significant clues to demonstrate how the loneliness mitigation is progressing and how to improve senior health in the long run.

Figure 17:
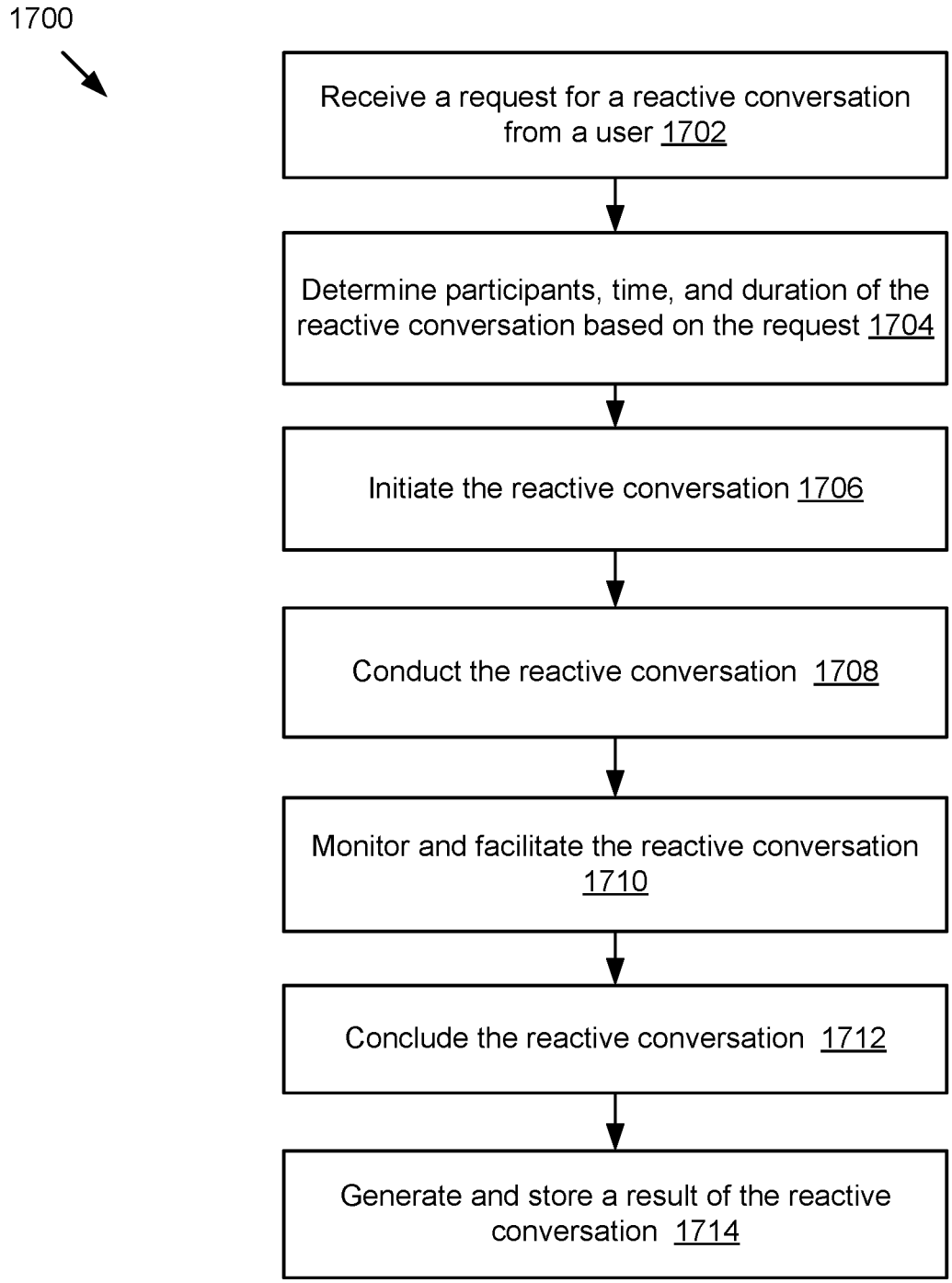
FIG. 17 is a flowchart of an example method for executing a reactive conversation.

FIG. 17 is a flowchart of an example method 1700 for executing a reactive conversation. At step 1702, the scheduler 259 receives a request for a reactive conversation from a user. A reactive conversation is a conversation that is initiated by a user of the system 100. A senior/user typically starts such a conversation by pressing a button on the VVA

101 or by speaking a prompt to the VVA 101 such as "Care system, Call Mike Mellow, I want to talk with him for ten minutes about Nicky's new baby." This user input is taken by the scheduler 259 as a trigger event or a conversation request to initiate a conversation.

At step 1704, the conversation setup manager 261 determines participants, time, and duration of the reactive conversation based on the request at step 1704. For example, when the senior/user presses the button on the VVA 101, the conversation setup manager 261 generates and presents questions to the senior/user to determine who the senior/user would like to talk to, when the senior/user would like to talk with them and for long the senior/user would like the conversation to be.

At step 1706, the conversation initiator 263 initiates the reactive conversation. For example, responsive to the conversation request, i.e., the spoken command or the button press, and responsive to the participant information received from the conversation setup manager 261, the conversation initiator 263 invites the requested participant(s) (e.g., Mike Mellow) to join the conversation through the VVA(s) 101 associated with the participant(s) and confirms that the participant(s) would like to talk with the senior/user (e.g., Mary Smith).

At step 1708, the conversation conducting module 265 conducts the reactive conversation. For example, the conversation conducting module 265 greets the participant(s), announces their arrival in the conversation, such as "Mary, Mike is on the line," and maintains an open connection with the VVA 101 associated with each participant for the duration of the conversation.

At step 1710, the IMP 225 monitors and facilitates the reactive conversation. At step 1712, the conversation evaluator 227 concludes the reactive conversation, and at step 1714, the conversation evaluator 227 generates and stores a result of the reactive conversation. In parallel with the conversation, the IMP 225 and the conversation evaluator 227 monitor what's being said, and whether the time to go is reached. When a TTG notification is generated, the conversation evaluator 227 concludes the conversation and stores the conversation object associated with the conversation in the database 208. The conversation object may include participant information, dialog acts, previous conversations the participant(s) participated in, description of the current conversation (e.g., the topics discussed, discussion time of each topic, duration of the conversation), etc.

Figure 18A:
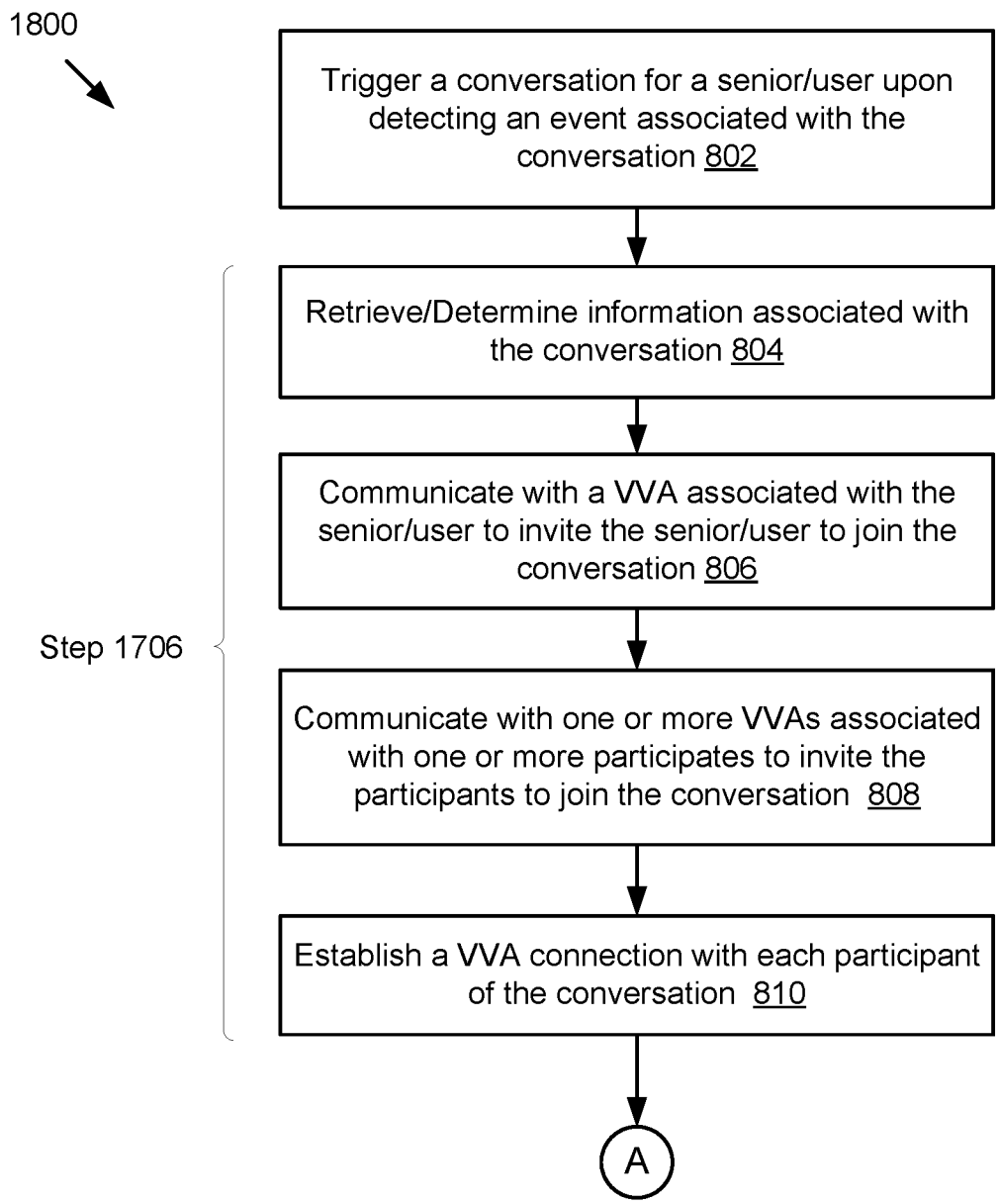
FIGS. 18A-18C are a flowchart of another example method for executing a proactive conversation.
Figure 18B:
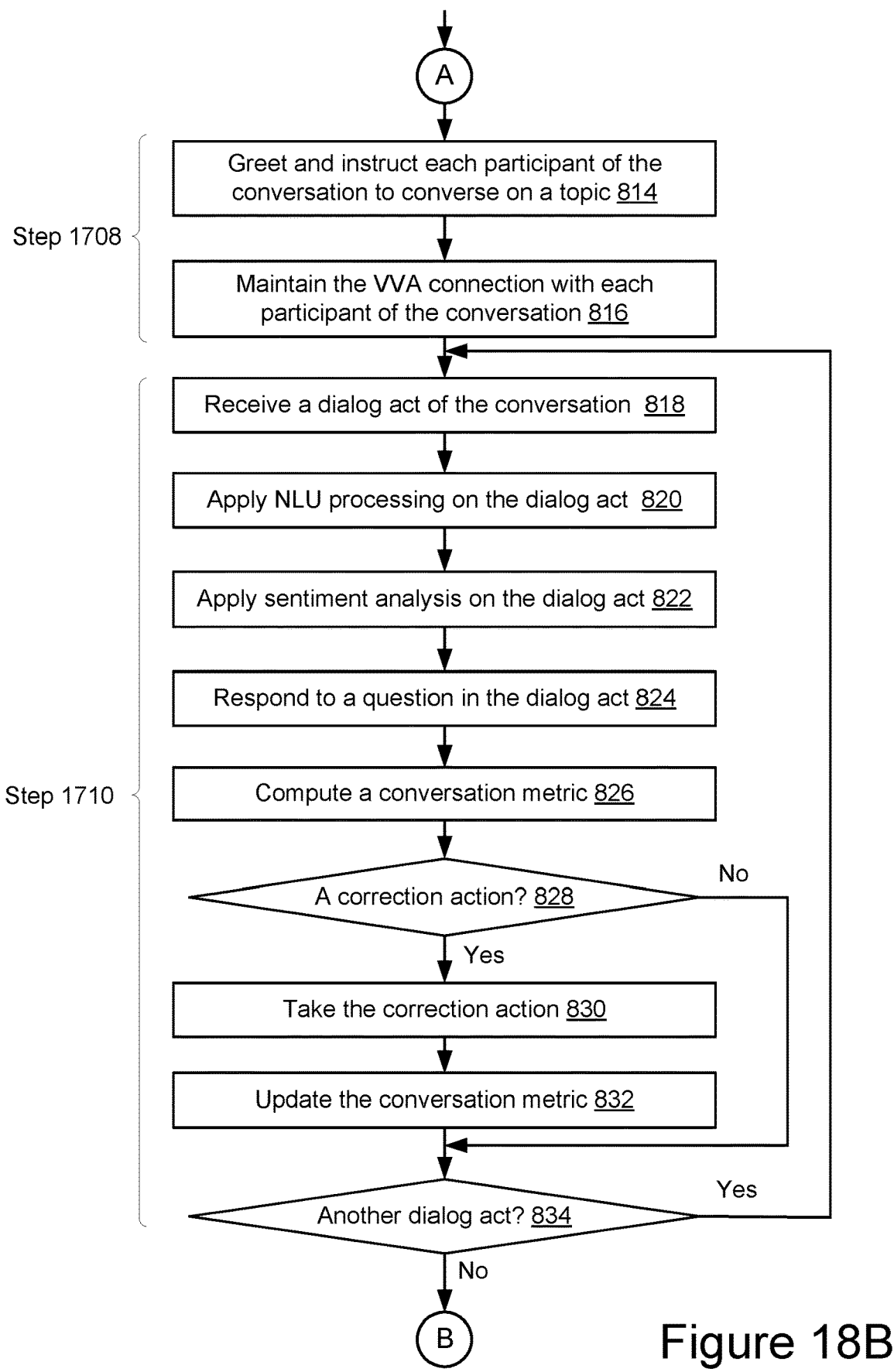
Figure 18C:
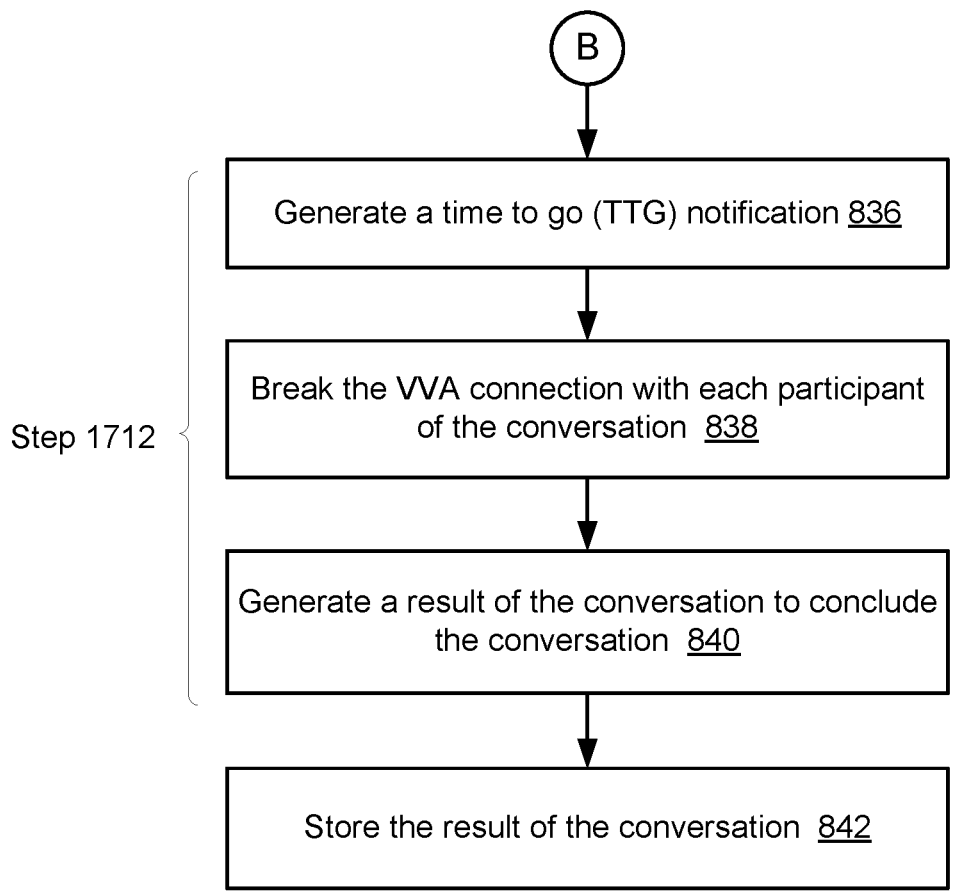

FIGS. 18A-18C illustrate a flowchart of another example method 1800 for executing a reactive conversation. The steps shown in these figures share high similarity with the steps for executing a proactive conversation as described in FIGS. 8A-8C. Therefore these figures are illustrated with same reference numbers as in FIGS. 8A-8C, and will not be repeatedly described herein. However, it should be noted that, because the reactive conversation is not requested by a requestor other than a senior/user and the conversation setup information (e.g., participant information, duration, time of the conversation) is determined based on the user request for the reactive conversation, FIGS. 18A-18C do not include steps 812 and 844. At step 812, conversation-based natural language understanding training is performed at the initiation stage of the conversation to determine the conversation setup information. At step 844, the requestor is notified of the result of the conversation.

Figure 19:
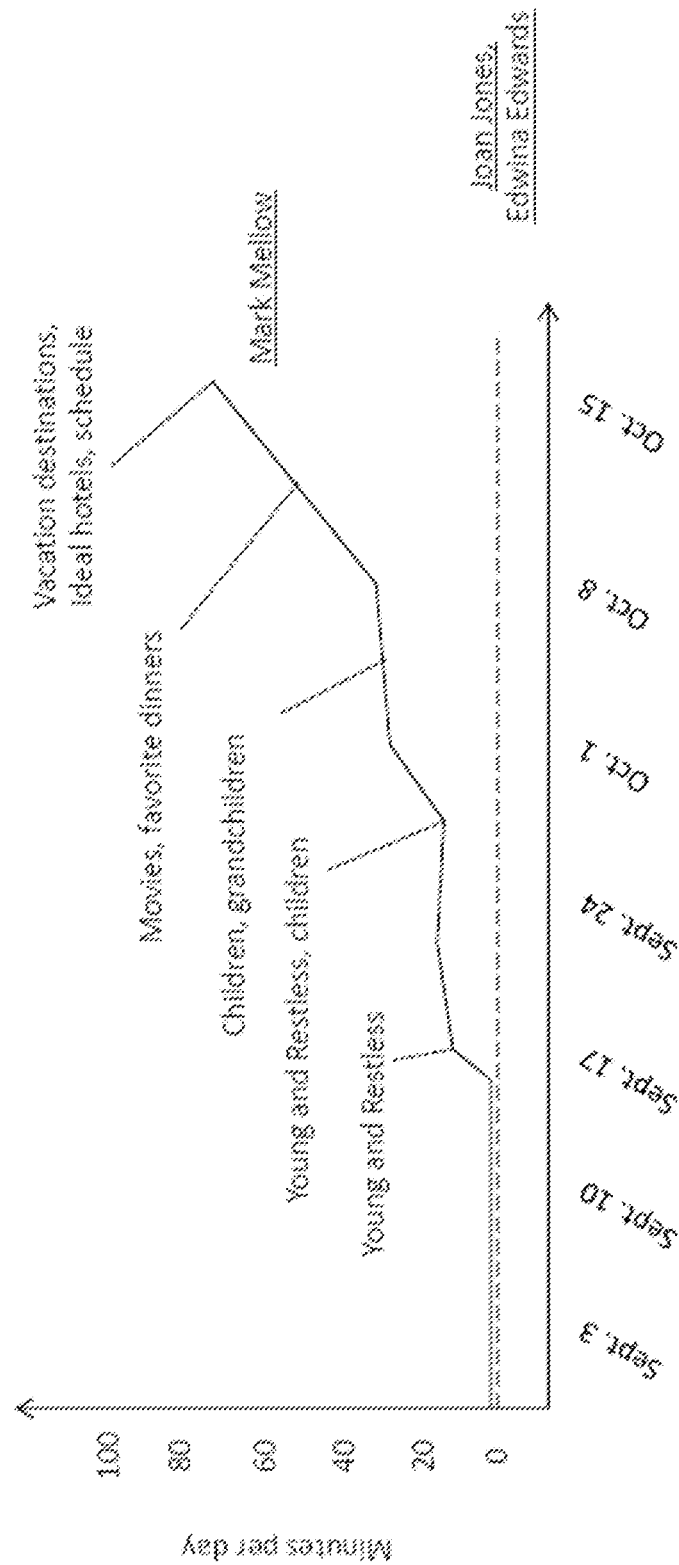
FIG. 19 is an example of an external contacts report.

FIG. 19 shows an example of an external contacts report. This report is generated by the conversation evaluator 227 from the reactive conversation initiated by Mary Smith as a result of her involvement in a 30-minute daily discussion of the Young and Restless with Joan Jones, Edwina Edwards, and Mark Mellow. The report indicates that Mary had no external contact outside of their regular Young and Restless discussion with either Joan or Edwina between September 3 and October 15. However, on about September 17, she started speaking with Mike Mellow for about 10 minutes per day about the Young and Restless. On about September 29 they started discussing their children. On October 1, they started talking about 25 minutes per day about their children and grandchildren. Between October 8 and October 15, their daily discussions ramped up to over 60 minutes per day and the topics included movies, favorite dinners, vacation destinations, ideal hotels, and a schedule for a possible vacation together. The report in FIG. 19 indicates that Mary Smith becomes more social and active as the group conversation continues over time, and thus achieves the goal of mitigating loneliness of the senior Mary Smith.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

To ease description, some elements of the system and/or the methods are referred to using the labels first, second, third, etc. These labels are intended to help to distinguish the elements but do not necessarily imply any particular order or ranking unless indicated otherwise.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Various implementations described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of an entirely hardware implementation, an entirely software implementation, or implementations containing both hardware and software elements. For instance, the technology may be implemented in software, which includes but is not limited to firmware, resident software, microcode, etc. Furthermore, the technology can take the form of a computer program object accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and Modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), WebSocket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats. Furthermore, the modules, routines, features, attributes, methodologies and other aspects of the disclosure can be implemented as software, hardware, firmware, or any combination of the foregoing. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment.

What is claimed is:

1. A system, comprising:
   one or more procesors;
   a memory storing one or more instructions that, when executed, cause the one or more processors to implement operations including:
   identifying, with the one or more processors, a senior at risk of loneliness;
   setting up a conversation of a plurality of human participants, wherein the plurality of human participants includes a senior at risk of loneliness;
   identifying at least one of a subject for the conversation and a set of questions for the conversation;
   monitoring, with the one or more processors, the conversation;
   tracking, with the one or more processors, a topic of the conversation;
   tracking, with the one or more processors, a mood of at least one participant of the conversation; and
   generating, with the one or more processors, a conversation prompt, in response to the topic and mood, to intervene in the conversation and facilitate mitigation of loneliness in the senior at risk of loneliness.

2. The system of claim 1, wherein the conversation prompt comprises a generic conversation prompt.

3. The system of claim 1, wherein the conversation prompt comprises a subject specific prompt related to a current subject under discussion.

4. The system of claim 1, wherein the conversation prompt comprises a new subject prompt.

5. The system of claim 1, wherein the conversation prompt comprises a joke.

6. The system of claim 1, further comprising applying sentiment analysis on the dialog act and using the sentiment analysis to track the mood of the conversation.

7. The system of claim 1, further comprising proactively initiating the conversation to mitigate loneliness in a senior at risk of loneliness based upon detecting a risk factor for loneliness in the senior.

8. The system of claim 1, further comprising generating, prior to the conversation of the plurality of human participants, a set of questions to structure the conversation to mitigate loneliness.

9. The system of claim 1, further comprising the system generating, prior to the conversation of the plurality of human participants, at least one subject for the conversation.

10. The system of claim 1, wherein the system generates, prior to the conversation of the plurality of human participants, a set of questions to structure the conversation to mitigate loneliness.

11. The system of claim 1, wherein the system generates a subject of interest for the conversation.

12. A computer-implemented method comprising:
   identifying that a senior is at risk of loneliness;
   setting up a conversation of a plurality of human participants, wherein the plurality of human participants includes the senior at risk of loneliness;
   monitoring, with one or more processors, the conversation of the plurality of human participants, wherein the plurality of human participants includes a senior at risk of loneliness;
   tracking, with the one or more processors, a topic of the conversation;
   tracking, with the one or more processors, a mood of at least one participant of the conversation; and
   generating, with the one or more processors, a conversation prompt, in response to the topic and mood, to intervene in the conversation and facilitate mitigation of loneliness in the senior at risk of loneliness.

13. The method of claim 12, wherein sentiment analysis is performed to track the mood of the conversation.

14. The method of claim 12, further comprising proactively initiating the conversation to mitigate loneliness in a senior at risk of loneliness based upon detecting a risk factor for loneliness in the senior.

15. The method of claim 12, further comprising generating, prior to the conversation of the plurality of human participants, a set of questions to structure the conversation to mitigate loneliness.

16. The method of claim 12, further comprising generating a subject of interest for the conversation.

\* \* \* \* \*